(12) United States Patent
Dow

(10) Patent No.: US 11,633,391 B2
(45) Date of Patent: *Apr. 25, 2023

(54) METHODS FOR THE TREATMENT AND PREVENTION OF LUNG INFECTIONS CAUSED BY GRAM-POSITIVE BACTERIA, FUNGUS, OR VIRUS BY ADMINISTRATION OF TAFENOQUINE

(71) Applicant: 60 Degrees Pharmaceuticals LLC, Washington, DC (US)

(72) Inventor: Geoffrey S. Dow, Washington, DC (US)

(73) Assignee: 60 Degrees Pharmaceuticals LLC, Washington, DC (US)

(*) Notice: Subject to any disclaimer, the term of this patent is extended or adjusted under 35 U.S.C. 154(b) by 90 days.

This patent is subject to a terminal disclaimer.

(21) Appl. No.: 17/189,544

(22) Filed: Mar. 2, 2021

(65) Prior Publication Data
US 2021/0267963 A1 Sep. 2, 2021

Related U.S. Application Data

(60) Provisional application No. 62/983,963, filed on Mar. 2, 2020, provisional application No. 63/031,466, filed on May 28, 2020, provisional application No. 63/032,836, filed on Jun. 1, 2020, provisional application No. 63/048,861, filed on Jul. 7, 2020, provisional application No. 63/072,052, filed on Aug. 28, 2020, provisional application No. 63/078,354, filed on Sep. 15, 2020, provisional application No. 63/079,804, filed on Sep. 17, 2020, provisional application No. 63/113,524, filed on Nov. 13, 2020.

(51) Int. Cl.
*A61K 31/4706* (2006.01)
*A61P 31/04* (2006.01)

(52) U.S. Cl.
CPC .......... *A61K 31/4706* (2013.01); *A61P 31/04* (2018.01)

(58) Field of Classification Search
None
See application file for complete search history.

(56) References Cited

U.S. PATENT DOCUMENTS 10,342,791 B2 7/2019 Smith et al.
2015/0099008 A1 4/2015 Curry et al.

OTHER PUBLICATIONS

U.S. Appl. No. 17/683,718, filed Mar. 2022, Dow; Geoffrey S.*
*Antimicrobial Agents and Chemotherapy*, 49(1) Antimicrobial Agents and Chemotherapy 1-20 (Jan. 2005).

Anttila et al., *Cytochrome P450-Mediated Pulmonary Metabolism of Carcinogens*, 44 Am. J. Respir. Cell Mol. Biol. 583-590 (2011).
Indonesia, 66(6) Am. J. Trop. Med. Hyg. 659-660 (2002).
Baird et al., *Short Report: Therapeutic Efficacy of Chloroquine Combined with Primaquine Against Plasmodium Falciparum in Northeastern Papua, Indonesia*, 66(6) Am. J. Trop. Med. Hyg. 659-660 (2002).
Barnes et al., *Aspergillosis: Spectrum of Disease, Diagnosis, and Treatment*, 20 Infectious Disease Clinics of North America 545-561 (2006).
Bartlett et al., *8-Aminoquinoiines from Walter Reed Army Institute for Research for Treatment and Prophylaxis of Pneumocystis Pneumonia in Rat Models*, 35(2) Antimicrobial Agents and Chemotherapy 277-282 (Feb. 1991).
Berge et al., *Pharmaceutical Salts*, 66(1) Journal of Pharmaceutical Sciences 1-19 (Jan. 1977).
Boshoff et al., *Biosynthesis and Recycling of Nicotinamide Cofactors in Mycobacterium tuberculosis*, 283(28) The Journal of Biological Chemistry 19329-19341 (Jul. 11, 2008).
Bowman et al., *Quantitative PCR Assay to Measure Aspergillus fumigatus Burden in a Murine Model of Disseminated Aspergillosis: Demonstration of Efficacy of Caspofungin Acetate*, 45(12) Antimicrobial Agents and Chemotherapy 3474-3481 (Dec. 2001).
Burrows et al., *Antimalarial drug discovery—the path towards eradication*, 141 Parasitology 128-139 (2014).
Camarda et al., *Antimalarial activity of primaquine operates via a two-step biochemical relay*, 10(3226) Nature Communications 1-9 (2019).
Chorin et al., *QT interval prolongation and torsade de pointes in patients with COVID-19 treated with hydroxychloroquine/azithromycin*, 17(9) Heart Rhythm 1425-1433 (2020).
Cillóniz et al., *Pneumocystis pneumonia in the twenty-first century: HIV-infected versus HIV-uninfected patients*, 17(10) Expert Rev. Anti. Infect. Ther. 787-801 (Oct. 2019) (Abstract Only).
Das et al., *Antimalarial drugs trigger lysosome-mediated cell death in chronic lymphocytic leukemia (CLL) cells*, 70 Leukemia Research 79-86 (Jul. 2018).
De Lima Barros et al., *Sporothrix schenckii and Sporotrichosis*, 24(4) Clinical Microbiology Review 633-654 (Oct. 2011).
Dow et al., *Radical curative efficacy of tafenoquine combination regimens in Plasmodium cynomolgi-infected Rhesus monkeys (Macaca mulatta)*, 10(212) Malaria Journal 1-10 (2011).
Dow et al., *The blood schizonticidal activity of tafenoquine makes an essential contribution to its prophylactic efficacy in nonimmune subjects at the intended dose (200 mg)*, 16(209) Malaria Journal 1-9 (2017).

(Continued)

*Primary Examiner* — Michael Barker
(74) *Attorney, Agent, or Firm* — Panitch Schwarze Belisario & Nadel LLP; Stephany G. Small; Erin M. Dunston

(57) ABSTRACT

Methods and composition for treating or preventing a lung infection, or related symptoms, caused by a bacterium, fungus, and/or virus using an effective amount of tafenoquine are disclosed. Methods and compositions for treating or preventing a lung infection in a human that is infected with SARS-CoV-2 using tafenoquine are disclosed.

47 Claims, 9 Drawing Sheets

Figures 1A, 1B:
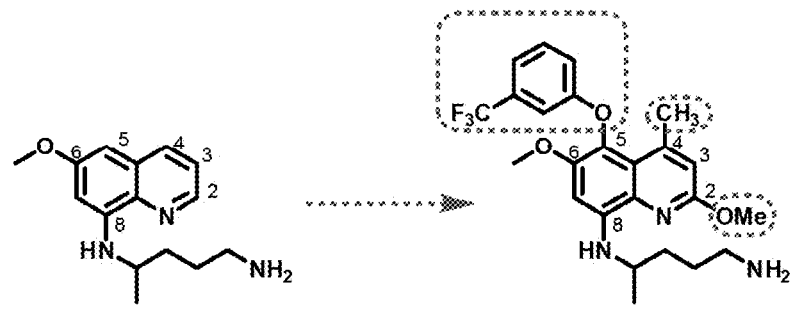

Specification includes a Sequence Listing.

(56) References Cited

OTHER PUBLICATIONS

Džimbeg et al., *The novel primaquine derivatives of N-alkyl, cydoalkyl or aryl urea: Synthesis, cytostatic and antiviral activity evaluations*, 43 European Journal of Medicinal Chemistry 1180-1187 (2008).
Ferreira-Coimbra et al., *Burden of Community-Acquired Pneumonia and Unmet Clinical Needs*, 37 Adv. Ther. 1302-1318 (2020).
Green et al., *Tafenoquine at Therapeutic Concentrations Does Not Prolong Fridericia-Corrected QT Internal in Healthy Subjects*, 54(9) The Journal of Clinical Pharmacology 995-1005 (2014).
Hall et al., *Immunohistochemical localization of NADPH-cytochrome P450 reductase in human tissues*, 10(3) Carcinogenesis 521-530 (Mar. 1989).
Hartline et al., *A standardized approach to the evaluation of antivirals against DNA viruses: Orthopox-, adeno-, and herpesviruses*, 159 Antiviral Research 104-112 (Nov. 2018) (Abstract Only).
Hoffmann et al., *Chloroquine does not inhibit infection of human lung cells with SARS-CoV-2*, 585 Nature 588-590 (2020).
International Search Report and Written Opinion dated May 24, 2021 in international Application No. PCT/US2021/020376.
Jean et al., *Epidemiology, Treatment, and Prevention of Nosocomial Bacterial Pneumonia*, 9(275) Journal of Clinical Medicine 1-21 (2020).
Keith et al., *A standardized approach to the evaluation of antivirals against DNA viruses: Polyomaviruses and lymphotropic herpesviruses*, 159 Antiviral Research 122-129 (Nov. 2018) (Abstract Only).
Keyaerts et al., *Antiviral Activity of Chloroquine against Human Coronavirus OC43 Infection in Newborn Mice*, 53(8) Antimicrobial Agents and Chemotherapy 3416-3421 (Aug. 2009).
Llanos-Cuentas et al., *Tafenoquine versus Primaquine to Prevent Relapse of Plasmodium vivax Malaria*, 380 The New England of Medicine 229-241 (2019).
Mahévas et al., Clinical efficacy of hydroxychloroquine in patients with covid-19 pneumonia who require oxygen: observational comparative study using routine care data, 369(M1844) BMJ 1-17 (May 14, 2020).
McCarthy et al., *Blood Schizonticidal Activity and Safety of Tafenoquine When Administered as Chemoprophylaxis to Healthy, Nonimmune Participants Followed by Blood Stage Plasmodium falciparum Challenge: A Randomized, Double-blind, Placebo-controlled Phase 1b Study*, 69 Clinical Infectious Diseases 480-486 (Aug. 1, 2019).
Mehra et al., *Retraction-Hydroxychloroquine or chloroquine with or without a macrolide for treatment of COVID-19: a multinational registry analysis*, 395 The Lancet 1820 (Jun. 13, 2020).
Mordue et al., *Could the Drug Tafenoquine Revolutionize Treatment of Babesia microti infection?*, 220 Journal of Infectious Diseases 442-447 (2019).
Oh et al., *Discovery and Structure-Activity-Relationship Study of N-Alkyl-5-hydroxypyrimidinone Carboxamides as Novel Antitubercular Agents Targeting Decaprenylphosphoryl-β-D-ribose 2'-Oxidase*, 61 Journal of Medicinal Chemistry 9952-9965 (2018).
Prashar et al., *Tafenoquine: A New 8-Aminoquinoline*, 36(4) Medical Journal of Zambia 187-190 (2009).
Prichard et al., *Activity and Mechanism of Action of N-Methanocarbathymidine against Herpesvirus and Orthopoxvirus Infections*, 50(4) Antimicrobial Agents and Chemotherapy 1336-1341 (Apr. 2006).
Prichard et al., *Benzimidazole Analogs inhibit Human Herpesvirus 6 V*, 55(5) Antimicrobial Agents and Chemotherapy 2442-2445 (May 2011) (Abstract Only).
Queener et al., *Efficacy of intermittent dosage of 8-aminoquinolines for therapy or prophylaxis of Pneumocystis pneumonia in rats*, 165(4) Journal of Infectious Diseases 764-768 (1992) (Abstract Only).
Rajic et al., *Asymmetric Primaquine and Halogenaniline Fumardiamides as Novel Biologically Active Michael Acceptors*, 23(1724) Molecules 1-18 (2018).
Rosenke et al., *Hydroxychloroquine Proves Ineffective in Hamsters and Macaques Infected with SARS-CoV-2*, https://dci.org/10.1101/2020.06.10.145144, this version posted Jun. 11, 2020, 23 pages.
Sheppard et al., *Novel inhalational Murine Model of Invasive Pulmonary Aspergillosis*, 48(5) Antimicrobial Agents and Chemotherapy 1908-1911 (May 2004).
Sheppard et al., *Standardization of an Experimental Murine Model of Invasive Pulmonary Aspergillosis*, 50(10) Antimicrobial Agents and Chemotherapy 3501-3503 (Oct. 2006).
Skipper et al., *Hydroxychloroquine in Nonhospitalized Adults With Early COVID-19*, Annals of Internal Medicine, pp. 1-10 (Jul. 16, 2020).
Tang et al., *Hydroxychloroquine in patients with mainly mild to moderate coronavirus disease 2019: open label, randomised controlled trial*, 369(m1849) BMJ 1-20 (2020).
Wang et al., *Remdesivir and chloroquine effectively inhibit the recently emerged novel coronavirus (2019-nCoV) in vitro*, 30 Cell Research 269-271 (2020).
Wayne et al., *An In Vitro Model for Sequential Study of Shiftdown of Mycobacterium tuberculosis through Two Stages of Nonreplicating Persistence*, 64(6) Infection and Immunity 2062-2069 (Jun. 1996).
Wiederhold et al., *Pharmacodynamics of Caspofungin in a Murine Model of Invasive Pulmonary Aspergillosis: Evidence of Concentration-Dependent Activity*, 190 Journal of Infectious Diseases 1464-1471 (2004).
Wiederhold et al., *Pyrosequencing to Detect Mutations in FKS1 that Confer Reduced Echinocandin Susceptibility in Candida albicans V*, 52(11) Antimicrobial Agents and Chemotherapy 4145-4148 (Nov. 2008).
Yao et al., *In Vitro Antiviral Activity and Projection of Optimized Dosing Design of Hydroxychloroquine for the Treatment of Severe Acute Respiratory Syndrome Coronavirus 2 (SARS-CoV-2)*, Infectious Diseases Society of America 1-25 (2020).

\* cited by examiner

| Molecule | Primaquine | Tafenoquine |
|---|---|---|
| Half-Life in Humans | 6 hours | 14 days |
| Activity Against Pf *in vivo* | No | Yes |
| Monotherapy for Pneumocystis | No | Yes |
| Dose for Clearance of Babesiosis | 100 mg/kg | 20 mg/kg |

Drug name: Tafenoquine succinate

Raw Data

| [sample] | units | Total Cells^ avgPOC | % Infection avgPOC |
|---|---|---|---|
| 0.003 | uM | 91.91 | 69.81 |
| 0.012 | uM | 96.39 | 109.24 |
| 0.049 | uM | 95.58 | 136.10 |
| 0.195 | uM | 89.88 | 145.24 |
| 0.781 | uM | 89.05 | 127.49 |
| 3.125 | uM | 102.07 | 112.12 |
| 12.500 | uM | 104.53 | 33.28 |
| 50.000 | uM | 13.30 | 0.58 |

^ Values represent Average Percentage of Control (POC)=(sample well measurement/aggregated DMSOavg)*100 for n=3.

FIG. 5

| Group | Vehicle Control | Tafenoquine 2.5 mg/kg | Tafenoquine 5 mg/kg | Posaconazole 20 mg/kg | Uninfected Control |
|---|---|---|---|---|---|
| Median Survival | 7 days | 6.5 days | 6 days | >12 days $p = 0.0006$ | >12 days |
| Percent Survival | 0% | 0% | 0% | 80% $p = 0.0007$ | 100% | p-value vs. Vehicle Control

| Group | 1 hr SAC | Vehicle Control | Tafenoquine 2.5 mg/kg | Tafenoquine 5 mg/kg | Posaconazole 20 mg/kg | Uninfected Control |
|---|---|---|---|---|---|---|
| Mean log₁₀ CFU/g (SD) | 4.14 (0.29) | 4.41 (0.34) | 4.36 (0.21) | 4.06 (0.54) | 3.28 (0.32) $p<0.0001$ | 0.0 (0) | p-value vs. Vehicle Control

SEQUENCE LISTING

```
<160> NUMBER OF SEQ ID NOS: 6

<210> SEQ ID NO 1
<211> LENGTH: 24
<212> TYPE: DNA
<213> ORGANISM: Mouse cytomegalovirus 1

<400> SEQUENCE: 1
tcagccatca actctgctac caac                                      24

<210> SEQ ID NO 2
<211> LENGTH: 26
<212> TYPE: DNA
<213> ORGANISM: Mouse cytomegalovirus 1

<400> SEQUENCE: 2
atctgaaaca gccgtatatc atcttg                                    26

<210> SEQ ID NO 3
<211> LENGTH: 33
<212> TYPE: DNA
<213> ORGANISM: Mouse cytomegalovirus 1

<400> SEQUENCE: 3
ttctctgtca gctagccaat gatatcttcg agc                            33

<210> SEQ ID NO 4
<211> LENGTH: 22
<212> TYPE: DNA
<213> ORGANISM: Guinea pig cytomegalovirus

<400> SEQUENCE: 4
gaggtcgaga agctgatatt gg                                        22

<210> SEQ ID NO 5
<211> LENGTH: 22
<212> TYPE: DNA
<213> ORGANISM: Guinea pig cytomegalovirus

<400> SEQUENCE: 5
gtctcttcct atgcgggtta tc                                        22

<210> SEQ ID NO 6
<211> LENGTH: 24
<212> TYPE: DNA
<213> ORGANISM: Guinea pig cytomegalovirus

<400> SEQUENCE: 6
acgtcacttt gagggccaac tgat                                      24
```

METHODS FOR THE TREATMENT AND PREVENTION OF LUNG INFECTIONS CAUSED BY GRAM-POSITIVE BACTERIA, FUNGUS, OR VIRUS BY ADMINISTRATION OF TAFENOQUINE

CROSS-REFERENCE TO RELATED APPLICATION

The present application claims the benefit of U.S. Provisional Application Ser. No. 62/983,963, filed Mar. 2, 2020, U.S. Provisional Application Ser. No. 63/031,466, filed May 28, 2020, U.S. Provisional Application Ser. No. 63/032,836 filed Jun. 1, 2020, U.S. Provisional Application Ser. No. 63/048,861 filed Jul. 7, 2020, U.S. Provisional Application Ser. No. 63/072,052, filed Aug. 28, 2020, U.S. Provisional Application Ser. No. 63/078,354, filed Sep. 15, 2020, U.S. Provisional Application Ser. No. 63/079,804, filed Sep. 17, 2020, and U.S. Provisional Application Ser. No. 63/113,524, filed Nov. 13, 2020 which are hereby incorporated by reference herein in their entirety, including any figures, tables, nucleic acid sequences, amino acid sequences, or drawings.

REFERENCE TO SEQUENCE LISTING SUBMITTED ELECTRONICALLY

This application contains a sequence listing, which is submitted electronically via EFS-Web as an ASCII formatted sequence listing with a file name "689503-42U1 Sequence Listing", creation date of Mar. 2, 2021, and having a size of about 4 KB. The sequence listing submitted via EFS-Web is part of the specification and is herein incorporated by reference in its entirety.

BACKGROUND OF THE INVENTION

Micro-organism and virus associated lung diseases cause considerable morbidity and mortality. According to a World Health Organization report from 2020, tuberculosis, caused by *Mycobacterium tuberculosis*, causes 10 million new infections and 1.6 million deaths each year. Many lung pathogens, including Mycobacteria tuberculosis, are known to form a quiescent stage in the lung that may survive many years, reactivating infection. These stages are much more resistant to traditional antibiotics than the actively-dividing forms, which cause symptomatic disease. Lung diseases associated with non-tuberculosis mycobacteria have been reported.

At the time of writing, severe acute respiratory syndrome coronavirus 2 (SARS-CoV-2), the betacoronavirus responsible for causing coronavirus disease 2019 (COVID-19) disease, had infected more than 112 million people worldwide, killing more than 2.5 million. This is just the most recent of numerous respiratory virus pandemics caused by coronaviruses and influenza viruses throughout history. Additionally, other respiratory viruses such as respiratory syncytial virus, para-influenza viruses, rhinoviruses, etc., cause considerable morbidity and mortality due to seasonal or endemic transmission.

*Pneumocystis* pneumonia, caused by the parasitic fungus *Pneumocystis jirovecci* (formerly known as *Pneumocystis carinii*), has historically been the most common opportunistic infection in AIDS patients and is associated with 15% and up to 50% mortality rates in the HIV- and some non-HIV-infected populations, and is increasing in incidence each year amongst individuals taking immunosuppressive medications for chronic diseases [Cilloniz et al. 2019 EXPERT REV ANTI INFECT THER. 2019 October; 17(10): 787-801. Epub 2019 Oct. 4].

Other important opportunistic fungi associated with pneumonia or lung disease in immunosuppressed individuals include *Aspergillus, Sporothrix, Mucormycetes, Blastomyces, Coccidia* spp, *Cryptococcus neoformans, Cryptococcus gatti* and *Histoplasma* [Barnes P D, Marr K A, *Aspergillosis: spectrum of disease, diagnosis, and treatment*. INFECT DIS CLIN NORTH AM. 2006 September; 20(3):545-61, vi; Barros et al. 2011 *Sporothrix schenckii* and Sporotrichosis. CLINICAL MICROBIOLOGY REVIEWS. 2011 October; 24(4):633-54; CDC 2020 (cdc.gov/fungal/diseases/)]. These infections are contracted by inhaling non-replicating spores present in the environment.

Gram positive *Staphylococcus aureus* and Gram-negative *Pseudomonas* spp, *Acinetobacter* spp, *Escherichia coli, Klebsiella* spp, *Stenotrophomonas multiphilia, Chryseobacterium/Elizabethkingia* spp are the organisms responsible for the vast majority of hospital acquired (HAP) and ventilator acquired (VAP) pneumonia [Shio Shin et al. 2020. J. CLIN. MED. 9, 275 (Shio Shin et al.)]. VAP is associated with 9-27% of mechanically ventilated hospital patients and has a 20-50% case fatality rate [Shio Shin et al]. Although HAP is less severe, the incidence of severe complications such as empyema, septic shock, and multi-organ failure may be as high as 50%. The treatment and prevention of all of these conditions is circumscribed by wide-spread drug resistance [Shio Shin et al].

Community acquired pneumonia (CAP) occurs at rates as high as 80 per 10,000 persons and is associated with a mortality rate of 6-20% in hospitalized patients [Ferreira-Coimbra, J., et al., *Burden of Community-Acquired Pneumonia and Unmet Clinical Needs*. ADV THER 37, 1302-1318 (2020) (Ferreira-Coimbra et al)]. Bacterial pathogens associated at the highest frequency with CAP include *Staphylococcus aureas, Streptococcus pneumoniae* and other *Streptococcus* spp, *Chlamydia pneumoniae, Mycoplasma pneumoniae, Legionella pneumophilia, Heamophilus influenzae*, and *Moroxella catarrhalis*. The treatment and prevention of all of these conditions is circumscribed by wide-spread drug resistance [Ferreira-Coimbra et al].

There is an urgent need for methods of treating or preventing lung infections and associated symptoms, caused by bacteria, fungi, and/or viruses.

SUMMARY OF THE INVENTION

The present invention concerns the use of long half-life 8-aminoquinolines for the treatment or prevention of human lung infections, and/or associated symptoms thereof (e.g., morbidity and mortality), caused by gram positive bacterium, fungus, and/or virus, such as SARS-CoV-2. In some embodiments, the long half-life 8-aminoquinoline is tafenoquine.

One aspect of the invention pertains to compositions and methods for administering a long half-life 8-aminoquinoline that meet the unmet medical need for preventing or treating bacterial, viral, and/or fungal lung infections, including those caused by coronavirus, such as SARS-CoV-2. In further embodiments, the method further comprises administering a second agent, such as a drug, to the human subject. In particular embodiments, the human subject is glucose-6-phosphate dehydrogenase (G6PD)-normal.

In particular embodiments, the long half-life 8-aminoquinoline is tafenoquine, or a pharmaceutically acceptable salt thereof. The long half-life 8-aminoquinoline may be administered to the human subject as at least one initial (loading) dose. The method may include detecting the presence of the bacterial, viral, and/or fungal infection prior to administration of the long half-life 8-aminoquinoline. Any suitable method for diagnosing or testing of the bacterial, viral, and/or fungal infection can be used, and such methods are well known in the art, including nucleic acid assays.

For both methods of treatment of lung infection and methods of prevention of lung infections, the method comprises administering to said subject an effective amount of tafenoquine or a compound of Formula (I), a pharmaceutically-acceptable salt thereof, or a pharmaceutical composition comprising tafenoquine or a compound of Formula (I),

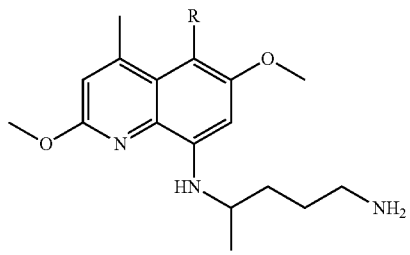

Formula (I)

wherein R is any halogen-containing substituent of molecular weight ≤205. In another embodiment, the lung infection is bacterial, viral, and/or fungal. In a further embodiment, the lung infection is caused by a bacterium, fungus, and/or virus. In another embodiment, the subject is a G6PD-normal human. In preferred embodiments, Formula (I) is tafenoquine. In other embodiments, the method comprises administering to said subject an effective amount of a second agent. In a further embodiment, the administration of tafenoquine or said compound of Formula (I) and administration of said second agent is concurrent. In yet other embodiments, the administration of said compound of Formula (I) and administration of said second agent is not concurrent. In even further embodiments, no second agent is administered.

In other embodiments, the second agent is selected from the group consisting of amikacin, an aminoglycoside, amoxicillin, amphotericin formulations, any drug approved by the Food and Drug Administration for treating or preventing bacterial viral, and/or fungal infections, any azole-containing anti-fungal drug, atovaquone, azithromycin, Bactrim, bedaquiline, a benzothiazinone, BTZ043, capreomycin, cefftriaxime, cefotaxime, cefuroxamine, clindamycin, clofazimine, corticosteroids, a cyclic peptide, cycloserine, delamanid, a diarylquinoline, echinocandin, ethambutol, ethionamide, fluconazole, flucytosine, a fluoroquinolone, an imidazopyridine amide, isoniazid, itraconazole, kanamycin, levofloxacin, linezolid, a macrolide, moxifloxacin, a nitroimidazole, an oxazolidinone, PA-824, para-aminosolicyclic acid, PBTZ169, posaconazole, prothionamide, pyrazinamide, Q203, quinine, rifampin, rifapentine, SQ-109, streptomycin, sulfa drugs, sutezolid, a thioamide, trimethoprimsulfamethoxazole, vancomycin, voriconazole, any anti-viral drug, remdesivir, favipiravir, chloroquine, hydroxychloroquine, a monoclonal antibody treatment, a steroid, COVID-19 convalescent plasma, casirivimab, imdevimab, bamlanivimab, baricitinib, interleukin-6 inhibitors, kinase inhibitors, tyrosine kinsase inhibitors, Tocilizumab, ivermectin, and any combination thereof.

In further embodiments, said lung infection may be sensitive, resistant, or multiply drug resistant to first- or second-line antimicrobials.

In other embodiments, the lung infection is tuberculosis, pneumonia, *pneumocystis* pneumonia, and/or due to Gram-positive bacteria. In another embodiment, the tuberculosis results from replicating and/or latent *Mycobacterium tuberculosis* infection. In further embodiments, the lung infection is an invasive Gram-positive bacterial infection caused by at least one bacteria selected from the list consisting of *Nocardia* spp, methicillin resistance and methicillin-sensitive *Staphylococcus aureus, Enterococcus* spp, coagulase negative *Staphylococcus*, and *Streptococcus* spp.

In other embodiments, said lung infection causes a disease selected from the group consisting of candidiasis, aspergillosis, fusariosis, cryptococcosis, trichosporonosis, mucormycosis or PCP. In further embodiments, said lung infection is caused by at least one fungus selected from the group consisting of *Aspergillus* spp. *Candida* spp. *Fusarium* spp, *Cryptococcus* spp, *Trichosporon* spp, *Rhizopus* spp, *Mucor* spp, *Rhizomucor* spp or *Lichtheimia* spp and *Pneumocystis*. In further embodiments the candidiasis is caused by azole-sensitive *Candida auris*, azole-resistant *C. auris*, echinochandin-sensitive *C. auris* and echinochandin-resistant *C. auris*, and/or *C. auris* resistant or sensitive to both azole and echinochandin.

In another embodiment, said lung infection is caused by a respiratory syncytial virus, para-influenza virus, rhinovirus, coronavirus, and/or an influenza virus. In further embodiments, the coronavirus is any variant of human coronavirus OC43 (HCoV-OC43) (β-CoV), human coronavirus HKU1 (HCoV-HKU1) (β-CoV), human coronavirus 229E (HCoV-229E) (α-CoV), human coronavirus NL63 (HCoV-NL63) (α-CoV), Middle East respiratory syndrome-related coronavirus (MERS-CoV) (β-CoV), severe acute respiratory syndrome coronavirus (SARS-CoV) (β-CoV), or SARS-CoV-2 (β-CoV).

In further embodiments said human subject with said lung infection and in particular embodiments said human has a coronavirus infection (e.g., SARS-CoV-2 infection), has one or more risk factors for disease progresses selected from the group consisting of: age of 60 years old or older, obesity, diabetes, and heart disease. In particular embodiments, said human subject has COVID-19 disease and has one or more risk factors for disease progresses selected from the group consisting of: age of 60 years old or older, obesity, diabetes, and heart disease. In other embodiments, the human subject with a lung infection has or is at risk of neutropenia.

In some embodiments, said subject has been confirmed to have bacterial, fungal and/or viral infection via laboratory test. In other embodiments, said subject is clinically suspected to have bacterial, fungal and/or viral infection. In additional embodiments, said bacterial, fungal, and/or viral infection includes at least one disease manifestation of infection selected from the group consisting of central nervous system, blood stream, skin, internal organ, and opthalmologic involvement.

In other embodiments, said subject is symptomatic of lung infection prior to the first administration. In other embodiments, said subject is symptomatic of a bacterial, fungal, and/or viral infection prior to the first administration. In particular embodiments, the human subject is symptomatic fora coronavirus infection (e.g., SARS-CoV-2 infection) at the time of first administration.

In other embodiments, said subject is asymptomatic of lung infection prior to the first administration. In other embodiments, said subject is asymptomatic of a bacterial, fungal, and/or viral infection prior to the first administration. In particular embodiments, the human subject is asymptomatic for a coronavirus infection (e.g., SARS-CoV-2 infection) at the time of first administration. In further embodiments, the human subject has tested positive for a coronavirus infection (e.g., SARS-CoV-2 infection) at the time of the administration but is asymptomatic. In particular embodiments, the human subject is asymptomatic for the coronavirus infection and/or has been diagnosed as coronavirus negative (e.g., SARS-CoV-2 negative) at the time of the administration. In other particular embodiments, the human subject has been exposed to coronavirus (e.g., SARS-CoV-2) or has had close contact with someone infected with the coronavirus (e.g., SARS-CoV-2).

In other embodiments, said lung infection is latent prior to the first administration.

In other embodiments, said subject is at risk of contracting a lung infection.

In other embodiments, the method is for preventing or treating invasive bacterial and/or fungal infections and associated morbidity and mortality in G6PD normal human subject occurring during or while in recovery from a corona viral infection (e.g., SARS-CoV-2 infection). In further embodiments, said human subject with corona viral infection has COVID-19 disease. In other embodiments, the method is for preventing or treating invasive bacterial and/or fungal infections in G6PD normal subject with suspected COVID-19 disease. In further embodiments said subject with a corona viral infection (e.g., SARS-CoV-2 infection) has or is at risk of neutropenia. In other embodiments, said subject with COVID-19 disease has or is at risk of neutropenia.

In further embodiments, said human subject has or is at risk of neutropenia. In other embodiments, said subject who has or is at risk of neutropenia has hematologic malignancies. In even further embodiments said subject who has or is at risk of neutropenia has received chemotherapy, is a transplant recipient under immunosuppressive treatment, is HIV positive with low T-cell counts, is experiencing other infectious diseases in which the immune system is suppressed, is taking courses of immunosuppressive medication including corticosteroids, and/or is taking antibody treatments for chronic diseases. In other embodiments, the transplant subject is receiving a bone marrow transplant, a heamatopietic stem cell transplant, or a solid organ transplant. In further embodiments, said subject has or is at risk of neutropenia, and/or is a transplant subject receiving a bone marrow transplant or a haematopoietic stem cell transplant or a solid organ transplant. In further embodiments, administration of tafenoquine to said subject comprises administration up to 90 days prior to transplantation or initiation of immunosuppressive therapy. For example, this may allow any minor hematologic changes associated with tafenoquine administration to normalize prior to transplantation or initiation of immunosuppressive therapy. In some embodiments, administration of tafenoquine comprises a dosing regimen of 200 mg/day for three days followed by 200 mg once weekly for as long as permitted by regulators. In other embodiments, administration of tafenoquine comprises the dose of tafenoquine as much as 399 mg at the same regimens as described herein, or as up to 8 doses as specified in Table 1 or Table 2.

In further embodiments, said human subject has at least one of the following conditions selected from the group consisting of: is at risk of catching respiratory virus during the winter season, [and therefore of contracting secondary infections], is elderly, is a surgical subject, has a catheter or iv line, has diabetes, has obesity, has COPD, has kidney disease, and has cardiac conditions. In further embodiments the subject is a child.

Yet another embodiment of the invention is a kit comprising: (a) a means for testing for G6PD deficiency; (b) tafenoquine or a compound of Formula (I), a pharmaceutically-acceptable salt thereof, or a pharmaceutical composition comprising tafenoquine or a compound of Formula (I); and

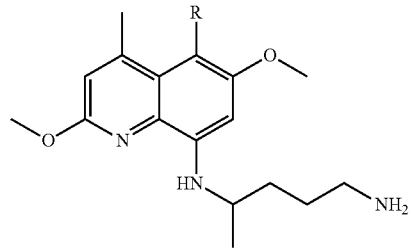

Formula (I)

(c) instructions for use, wherein R is any halogen-containing substituent of molecular weight ≤205. In another embodiment, such a kit further comprises (d) an effective amount of a second agent selected from the group consisting of amikacin, an aminoglycoside, amoxicillin, amphotericin formulations, any drug approved by the Food and Drug Administration for treating or preventing bacterial, viral, and/or fungal infections, any azole-containing anti-fungal drug, atovaquone, azithromycin, Bactrim, bedaquiline, a benzothiazinone, BTZ043, capreomycin, cefftriaxime, cefotaxime, cefuroxamine, clindamycin, clofazimine, corticosteroids, a cyclic peptide, cycloserine, delamanid, a diarylquinoline, echinocandin, ethambutol, ethionamide, fluconazole, flucytosine, a fluoroquinolone, an imidazopyridine amide, isoniazid, itraconazole, kanamycin, levofloxacin, linezolid, a macrolide, moxifloxacin, a nitroimidazole, an oxazolidinone, PA-824, para-aminosolicyclic acid, PBTZ169, posaconazole, prothionamide, pyrazinamide, Q203, quinine, rifampin, rifapentine, SQ-109, streptomycin, sulfa drugs, sutezolid, a thioamide, trimethoprimsulfamethoxazole, vancomycin, voriconazole, and any combination thereof.

In particular embodiments, said compound of Formula (I) is tafenoquine. In other particular embodiments, the long half-life 8-aminoquinoline is tafenoquine. In some embodiments, at least one dose of about 100 mg-600 mg of tafenoquine are administered. In another embodiment, at least seven doses of about 100 mg-600 mg of tafenoquine are administered. In other embodiments, administration is conducted according to the dosing regimen of any one of Tables 1-2 and/or according to any of the Examples. In other embodiments, no more than 10,800 mg is administered to said subject in a six-month period. In some embodiments, administration of tafenoquine comprises a dosing regimen of 200 mg/day for three days following by 200 mg once weekly for as long as permitted (e.g., permitted by regulators). In other embodiments, administration of tafenoquine comprises the dose of tafenoquine as much as 399 mg at the same regimens as described herein, or as up to 8 doses as specified in Table 1 or Table 2.

In other embodiments, the measured half-life of the compound of Formula (I) is at least three times greater than the measured half-life of primaquine. In other embodiments, the measured half-life or its metabolites in plasma or lung is at least three times longer than the measured half-life of primaquine in plasma or lung.

In other embodiments, said compound of Formula (I) is an 8-aminoquinoline with a measured half-life greater than primaquine. In other embodiments, the measured half-life of the 8-aminoquinoline or its metabolites in plasma or lung is longer than the measured half-life of primaquine in plasma or lung.

In other embodiments, administration is conducted such that gastro-intestinal disturbance in said subject is minimized. In other embodiments, administration is via sub-lingual and/or buccal route(s).

In further embodiments, Formula (I) is tafenoquine and administration comprises a loading dose every day for three days. In other embodiments, the long half-life 8-aminoquinoline is tafenoquine and administration comprises a loading dose every day for three days. In further embodiments the loading dose is 200 mg per day. In another embodiment, the human subject is administered 200 mg of tafenoquine once a day for three days and weekly 200 mg dose of tafenoquine. In certain embodiments, administration of oral dose of tafenoquine to the human subject is initiated once the human subject has recovered to the point where taking oral medications becomes feasible and wherein the dosing regimen is a loading dose for three days, followed by weekly doses for as long as permitted (e.g., by regulators). In further embodiments, said loading dose is 200 mg/day and the weekly doses is 200 mg per week. A further embodiment, administration of tafenoquine is a dose of as much as 399 mg and administered according to the regimens described herein, or as up to 8 doses as specified in Table 1 or Table 2. In particular embodiments, administration of tafenoquine prophylaxis is a loading dose of 200 mg every day for three days as soon as practicable following hospitalization for suspected COVID-19 disease but before symptom progression or requirement for mechanical ventilation make oral dosing feasible; for example if the 600 mg loading dose was completed but symptom progression or mechanical ventilation subsequently rendered oral dosing temporarily unfeasible for one week, and less than 14 days has passed since the end of the loading dose, tafenoquine prophylaxis could be re-initiated starting with a loading dose of 400 mg [200 mg/day for two days] then 200 mg weekly thereafter for as long as permitted by regulators; for example if the 600 mg loading dose was completed but symptom progression or mechanical ventilation subsequently rendered oral dosing temporarily unfeasible for one week, and less than 21 days has passed since the end of the loading dose, tafenoquine prophylaxis could be re-initiated starting with a loading dose of 600 mg [200 mg/day for three days] then 200 mg weekly thereafter for as long as permitted by regulators; for example if only 400 mg loading dose was completed but symptom progression or mechanical ventilation subsequently rendered oral dosing temporarily unfeasible for one week, and less than 7 days has passed since the end of the loading dose, tafenoquine prophylaxis could be re-initiated starting with a loading dose of 400 mg [200 mg/day for two days] then 200 mg weekly thereafter; and for example if only 200 mg loading dose was completed but symptom progression or mechanical ventilation subsequently rendered oral dosing temporarily unfeasible for two weeks, and less than 14 days has passed since the end of the loading dose, tafenoquine prophylaxis could be re-initiated starting with a loading dose of 600 mg [200 mg/day for three days] then 200 mg weekly thereafter for as long as permitted by regulators. In a further embodiment, administration of tafenoquine is a dose of as much as 399 mg and administered according to the regimens described herein, or as up to 8 doses as specified in Table 1 or Table 2.

Figures 9A, 9B:
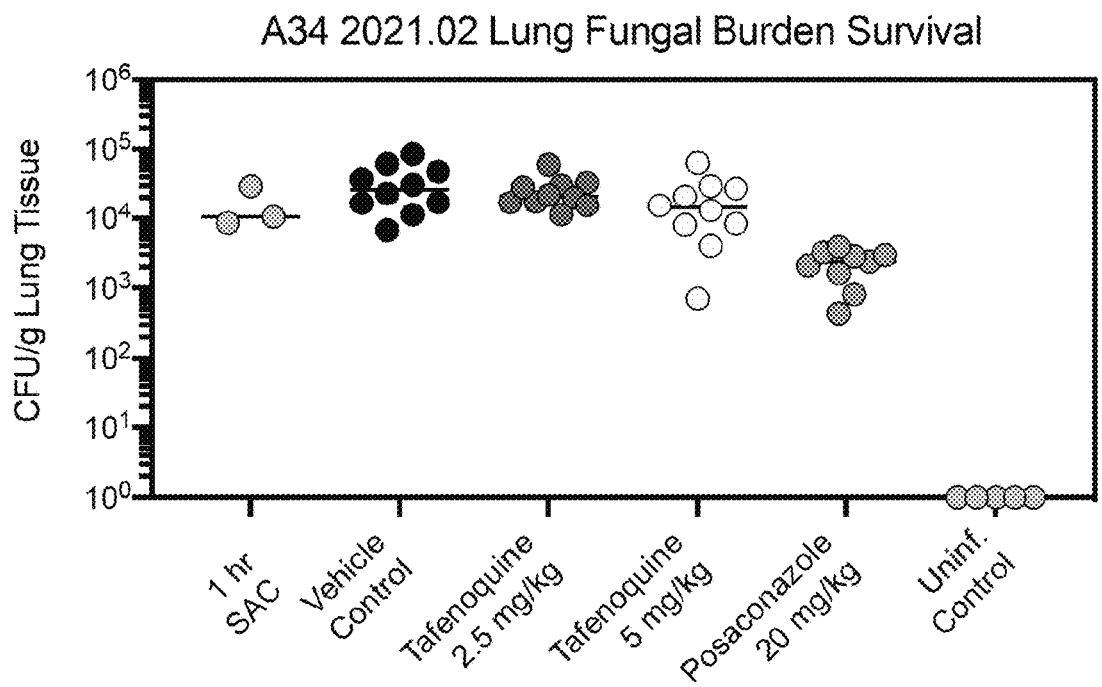

In other embodiments, the method is for preventing or treating anthrax or other Gram positive biodefence pathogens, wherein said subject is exposed to *B. anthracis* or other relevant Gram positive bacteria. In further embodiments, said subject is exposed to *B. anthracis* or other relevant Gram-positive bacteria through the occupation of said subject. In other embodiments, said subject has not received an effective vaccine. For example, for whom it is not possible to take a vaccine for medical or access reasons or whom any vaccine administered does not afford sufficient protection [e.g. if the vaccine efficacy is <80% or if there are clinical data demonstrating efficacy]. In some embodiments, tafenoquine would be administered to asymptomatic individuals. In some embodiments, administration of tafenoquine comprises a dosing regimen of 200 mg/day for three days following by 200 mg once weekly for as long as permitted by regulators. In other embodiments, administration of tafenoquine comprises the dose of tafenoquine as much as 399 mg at the same regimens as described herein, or as up to 8 doses as specified in Table 1 or Table 2.

In some embodiments, the long half-life 8-aminoquinoline is used to treat a patient with symptomatic SARS-CoV-2 or other human infection in whom symptoms of infection have persisted for no longer than five days. In particular embodiments a dose of 200 mg is administered on the first, second [+/− one day], third [+/− one day], and tenth [+/− one day] days.

BRIEF DESCRIPTION OF THE DRAWINGS

The foregoing will be apparent from the following more particular description of example embodiments of the invention, as illustrated in the accompanying drawings.

FIG. 1A and FIG. 1B: Molecular structure of primaquine and tafenoquine depicted together with summary biological data referenced in the text. Tafenoquine has a longer half-life in vivo and is consequently more potent with a broader spectrum of effects against multiple organisms.

FIG. 2: Desired structure of 8-aminoquinolines active against lung pathogens. R is any halogen-containing substituent of molecule weight ≤205.

FIG. 3: Concentration of tafenoquine in microgram equivalents per g of tissue in various tissues of male rats 12 h following administration of [14C]radio-labeled tafenoquine (25 mg base/kg). Radioactivity was measured in the combusted organs of euthanized rats by liquid scintillation analysis.

FIG. 4: In vitro antiviral SARS-CoV2 Data Report with Tafenoquine succinate. Dose response curves and analytic data including IC50s [in microM] for remdesivir and tafenoquine against SARS-CoV-2 in CALU cells in vitro. Herein IC50 is used interchangeably with EC50.

FIG. 5: In vitro antiviral SARS-CoV2 raw data report for tafenoquine in Calu3 cells.

FIG. 6: Mouse weights throughout the course of the study (days −2 through 8) of Example 28, Experiment 1.

FIG. 7: Mouse weights at the end of the observation period (days 7/8) of Example 28, Experiment 1.

FIG. 8A and FIG. 8B: Survival curves in neutropenic *Aspergillus* infected mice administered posoconazole or prophylactic tafenoquine.

FIG. 9A and FIG. 9B—Pulmonary fungal burden in neutropenic *Aspergillus* infected mice administered tafenoquine or Posaconazole.

DETAILED DESCRIPTION OF THE INVENTION

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

As used herein, the singular forms "a," "and," and "the" include plural reference unless the context clearly dictates otherwise. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc.

As used herein, the term "about" refers to a number that differs from the given number by less than 15%. In other embodiments, the term "about" indicates that the number differs from the given number by less than 14%, 13%, 12%, 11%, 10%, 9%, 8%, 7%, 6%, 5%, 4%, 3%, 2%, or 1%.

As used herein, "asymptomatic" refers to a human subject that may or may not have been exposed to a bacteria, fungus, and/or virus which may cause a lung infection and does not present symptoms related to a bacterial, fungal, and/or viral infection. An asymptomatic human subject may or may not be infected with a bacteria, fungus, and/or virus which may cause a lung infection. For example, an asymptomatic human subject includes a human subject that has no symptoms related to a SARS-CoV-2 infection and has been in close contact with someone that is infected with SARS-CoV-2. In another example, an asymptomatic human subject includes a human subject that has no symptoms related to a SARS-CoV-2 infection and has tested positive for infection of SARS-CoV-2.

As used herein, "G6PD" means Glucose-6-phosphate dehydrogenase and "G6PD deficiency" refers to a subject being deficient in this enzyme. In humans, treatment of a subject who has G6PD deficiency with an 8-aminoquinoline may cause hemolysis, which can be clinically significant in some cases.

As used herein, "G6PD-normal" refers to human subjects with normal levels of glucose-6-phosphate dehydrogenase. Normal levels of G6PD may be determined by approved laboratory tests using validated methodology known to those skilled in the art.

The human subject may be an adult or a child. As used herein, a "child" refers to a human subject who is between the ages of 1 day to 17 years of age. The term "adult" refers to a human subject who is 18 years of age or older.

As used herein, "loading phase" or "loading dose(s)" or "initial dose(s)" refers to the initial administration of the material and is at least one dose. For example, the loading phase may be once per day for three consecutive days or less prior to administration of less frequent administration of doses.

As used herein, "subsequent dose(s)" refers to doses administered after initial dose(s) and is at least one dose. The subsequent dose(s) may be the same amount or may be a different amount than the initial dose(s). The subsequent dose(s) may be administered in the same time frame or may be administered in a different time frame than the initial dose(s).

As used herein, "per day" means in a given 24-hour period.

As used herein, "per week" means in a given 7-day period.

"Three times a day dosing" or "three times per day," as used herein, refers to three administrations of a composition per every 24-hour period.

"Four times a day dosing" (QDS) or "four times per day," as used herein, refers to four administrations of a composition per every 24-hour period.

In particular, embodiments of the methods and compositions may use a pharmaceutical composition comprising a compound of Formula (I), or a pharmaceutically acceptable salt thereof. The disclosed compounds of Formula (I), or a pharmaceutically available salt thereof, can be administered to the subject in conjunction with an acceptable pharmaceutical carrier or diluent as part of a pharmaceutical composition for the methods described herein, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

"Pharmaceutically acceptable carrier" means non-therapeutic components that are of sufficient purity and quality for use in the formulation of a composition of the invention that, when appropriately administered, typically do not produce an adverse reaction, and that are used as a vehicle for a drug substance (e.g., a compound of Formula (I), such as tafenoquine).

The phrase "pharmaceutically acceptable" indicates that the substance or composition must be compatible chemically and/or toxicologically, with the other ingredients comprising a formulation, and/or the mammal being treated therewith.

Pharmaceutical formulations include "pharmaceutically acceptable" and "physiologically acceptable" carriers, diluents or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

The compounds of the present invention can be formulated into pharmaceutically-acceptable salt forms. Pharmaceutically-acceptable salts of the compounds of the invention can be prepared using conventional techniques.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The phrase "effective amount" means an amount of an agent, such as an alpha-glucosidase inhibitor, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a subject is "in need of" a treatment if such human or non-human animal subject would benefit biologically, medically or in quality of life from such treatment (preferably, a human).

As used herein, the term "inhibit", "inhibition" or "inhibiting" refers to the reduction or suppression of a given condition, symptom, or disorder, or disease (e.g., coronavirus infection, or coronavirus viral load or titer), or a significant decrease in the baseline activity of a biological activity or process (e.g., alpha-glucosidase production, inhibitors of glycoprotein processing, and inhibitors of alpha-glucosidase activity such as alpha-glucosidase I activity).

As used herein, a subject is "in need of" a treatment if such human subject would benefit biologically, medically or in quality of life from such treatment (preferably, a human). In some embodiments, the subject has a lung infection and is in need of therapy. In other embodiments, the subject does not have a lung infection and is in need of prophylaxis. In some embodiments, the subject in need of prophylaxis is at risk of becoming infected with a bacteria, fungus, and/or virus which may cause a lung infection. In some embodiments, the subject is at increased risk of becoming infected with a bacteria, fungus, and/or virus relative to others in the population.

As used herein, the terms "subject", "patient", and "individual" are used interchangeably and refer to a human of any age or gender.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, sub-lingual, buccal, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the meaning of the phrase "close contact" in the context of a human having been exposed to someone infected with a bacteria, fungus, and/or virus (e.g., SARS-CoV-2 or variant) will depend upon the exposure setting. The meaning may be the definition adopted by the government health agency having jurisdictional authority, and may be based on factors such as the presence of special populations. In some embodiments, close contact exists if the subject was within 6 feet of an infected person for a cumulative total of 15 minutes or more over a 24-hour period.

As used herein, "prevent" or "prevention" refers to achieving, partially, substantially, or completely, one or more of the following results: avoiding the disease, disorder, or syndrome resulting from a bacterial, fungal, and/or viral infection, (e.g., an infection from any variant of SARS-CoV-2, disease such as COVID-19); avoiding clinical symptom or indicator associated with a disease, disorder, or syndrome resulting from a bacterial, fungal, and/or viral infection (e.g., an infection from any variant of SARS-CoV-2); reducing the severity of the disease, disorder, or syndrome resulting from a bacterial, fungal, and/or viral infection (e.g., an infection of any variant of SARS-CoV-2); or avoiding a bacterial, fungal, and/or viral infection (e.g., an infection from any variant of SARS-CoV-2).

The terms "strain" and "variant" are used interchangeably herein to refer to subtypes of a microorganism (e.g., a virus, bacterium, or fungus) that are genetically distinct from each other. For example, SARS-CoV-2 has multiple variants currently circulating globally. Such SARS-CoV-2 variants include at least B.1.1.7 identified in the United Kingdom, B.1.351 identified in South Africa, and P.1 identified in travelers from Brazil. For example, SARS-CoV-2 variants may include mutations, such as the following: E484K, which was first discovered in the United Kingdom; L452R, which was detected in Denmark; and D614G discovered in China in January 2020. Other mutations identified in SARS-CoV-2 variants include, for example, the 69/70 deletion, 144Y deletion, N501Y, A570D, P681H, E484K, and K417N/T.

As used herein, "symptomatic" refers to a subject in whom symptoms of micro-organism-induced lung disease is evident upon clinical evaluation.

As used herein, "Coronavirus disease 2019" or "COVID-19" or "2019-nCoV acute respiratory disease" refers to the infectious disease caused by "severe acute respiratory syndrome coronavirus 2" also known as "SARS-CoV-2" or "Wuhan virus".

As used herein, "tafenoquine" refers to a compound of Formula (I) with the following structure:

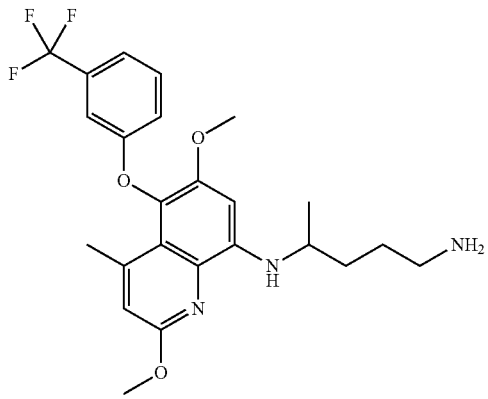 [SMILES: COc1cc(C)c2c(Oc3cccc(C(F)(F)F)c3)c(OC)cc(NC(C)CCCN)c2n1]

which has an alternative name of N(4)-[2,6-Dimethoxy-4-methyl-5-[3-(trifluoromethyl)phenoxy]quinolin-8-yl]pentane-1,4-diamine, or a pharmaceutical acceptable salt thereof. Tafenoquine may also be known as Tafenoquine [INN:BAN], Etaquine, UNII-262P8GS9L9, C24H28F3N3O3, CHEBI:172505, AIDS006901, 106635-81-8 (maleate), AIDS-006901, CID115358, SB-252263, WR 238605, WR-238605, WR238605, LS-172012, 1,4-Pentanediamine, N4-(2,6-dimethoxy-4-methyl-5-(3-(trifluromethyl)phenoxy)-8-quinolinyl-, 106635-80-7, N(4)-(2,6-Dimethoxy-4-methyl-5-((3-trifluromethyle)phenoxy)-8-quinolinyl)-1,4-pentanediamine, N-[2,6-dimethoxy-4-methyl-5-[3-(trifluoromethyl)phenoxy]quinolin-8-yl] diamine, (4-Amino-1-methylbutyl){2,6-dimethoxy-4-methyl-5-[3-(trifluoromethyl)phenoxy](8-quinoly)}amine, (R)—N3-(2,6-Dimethoxy-4-methyl-5-(3-trifluoromethyl)phenoxy)quinolin-8-yl)pentane-1,4-diamine, (RS)—N(sup 3)-(2,6-Dimethoxy-4-methyl-5-(3-trifluoro-methylphenoxy)quinolin-8-yl)pentane-1,4-diamine. A pharmaceutically acceptable salt thereof, including,

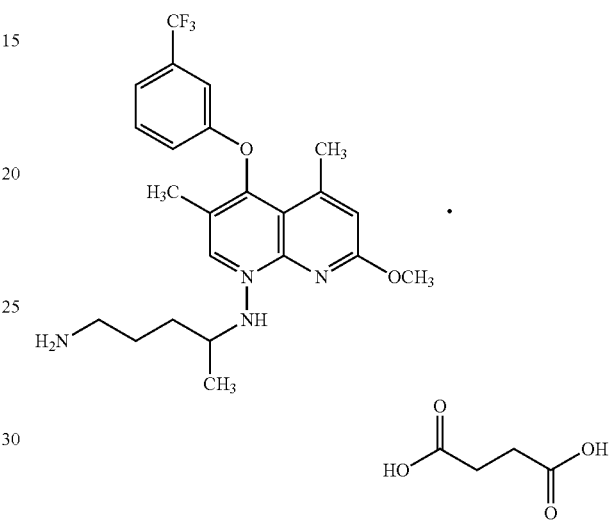

CAS number for above identified structure of succinate salt 106635-81-8.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention. The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt.

When used herein, a dose range reflected as two numbers means those doses as well as all doses within that range. For example, a dose range from 10 mg-11 mg means 10.0 mg, 10.05 mg, 10.10 mg, 10.15 mg, 10.20 mg, 10.25 mg, 10.30 mg, 10.35 mg, 10.40 mg, 10.45 mg, 10.50 mg, 10.55 mg, 10.60 mg, 10.65 mg, 10.70 mg, 10.75 mg, 10.80 mg, 10.85 mg, 10.90 mg, 10.95 mg, 11.00 mg, as well as any and all amounts therein, such as 10.34 mg, 10.78 mg, etc.

As used herein, "suspected COVID-19 disease" means a subject that has either been confirmed or not confirmed with a laboratory test for COVID-19 or who has been exposed to an individual with known or suspected COVID-19 disease.

Long Half-Life 8-Aminoquinolines

Tafenoquine and other long half-life 8-aminoquinolines offer a therapeutic and prophylactic alternative to the standard of care for viruses, gram-positive bacteria, and fungi which cause lung infections due to (i) an exceptionally long half-life that broadens their modes of action relative to short half-life 8-aminoquinolines such as primaquine, (ii) their exceptionally high accumulation in lung tissue relative to the blood compartment, (iii) their unique mode of action against quiescent (as well as replicating) life cycle stages given that many lung pathogens are associated with quiescent non-replicating or spore-forming stages (iv) the lack of demonstrated QTC prolongation in humans at therapeutically relevant doses and (v) effects on host-cell physiology that offers a mechanism of viral replication different or complementary to other quinolines.

8-aminoquinolines are known to target quiescent organisms such as the hypnozoites of *P. vivax* and the gametocytes of all malaria parasites [Llanos-Cuentos et al. 2019. N Engl J Med. 2019 Jan. 17; 380(3):229-241]. While many other anti-malarials, including tafenoquine and primaquine, target actively-dividing blood stages of malaria, only 8-aminoquinolines target the quiescent hypnozoites [Burrows et al. 2014. Parasitology. 2014 January; 141(1):128-39. Epub 2013 Jul. 17]. The mechanism of action of 8-aminoquinolines is thought to be via site specific activation to oxidative intermediates [Camarda et al 2019. Antimalarial activity of primaquine operates via a two-step biochemical relay. Nat Commun 10:3226 (Camarda et al 2019)]. Tafenoquine and other 8-aminoquinolines are active against both the quiescent and actively-dividing forms of *Mycobacterium* as well as other micro-organisms (with both replicating and non-replicating forms) associated with disease in humans and animals.

Extension of the half-life of 8-aminoquinolines through substitution at the 2, 4, and 5 positions of the quinoline ring is known to increase the potency and expand the spectrum of action compare to short half-life 8-aminoquinolines as primaquine. See FIG. 1A and FIG. 1B. For example, whereas primaquine has only week activity against the blood stages of *P. falciparum*, tafenoquine is quite effective [Baird et al. 2002. Am J Trop Med Hyg. 2002 June; 66(6):659-60; McCarthy et al. 2019. Clin Infect Ds. 2019 Jul. 18; 69(3): 480-486]. Similarly, whilst tafenoquine can be administered as monotherapy to cure *Pneumocystis* infections in mice, primaquine must be combined with clindamycin to achieve the same outcome [Bartlett et al. ANTIMICROBIAL AGENTS AND CHEMOTHERAPY, February 1991, Vol 35(2): 277-282 (Bartlett et al. 1991)]. Also, whereas single doses of 20 mg/kg tafenoquine cleared Babesia parasitemia in mice [Mordue and Wormser 2019. 442 jid 2019:220, 1 August], a much higher dose of primaquine is required [100 mg/kg, Yao et al. 2015. J Infect Dev Ctries. 2015 Sep. 27; 9(9):1004-10].

Chloroquine and the related drug hydroxychloroquine have been proposed for both prevention and treatment of SARS-CoV-2, based on the well characterized mechanism of host cell lysosomal protonation, in vitro activity against SARS-CoV-2, accumulation in the lungs [the presumed site of viral replication], and the well characterized safety profile over sixty or more years of use to treat and prevent malaria and inflammatory conditions [Yao et al., In Vitro Antiviral Activity and Projection of Optimized Dosing Design of Hydroxychloroquine for the Treatment of Severe Acute Respiratory Syndrome Coronavirus 2 (SARS-CoV-2). *Clin Infect Dis*. 2020 Mar. 9]. Data from two randomized studies and one large hospital registry study are available from hospitalized patients: The first of the these studies showed no difference in viral clearance compared to standard of care [Tang et al. BMJ May 14, 2020], the second showed no difference in requirement for ICU transfer in patients requiring oxygen [Mahevas et al BMJ May 14, 2020], and the third showed a higher rate of all-cause mortality including fatal cardiac arrythmias relative to the standard of care. Although these studies are not blinded, randomized, placebo-controlled investigations they have collectivity called into the question whether hydroxychloroquine is safe and effective in the general hospitalized COVID-19 population. Clinical trials were underway to evaluate the utility of chloroquine and hydroxychloroquine for prevention and treatment in an out-patient setting, but no results were available.

That hydroxychloroquine would cause cardiotoxicity in some individuals is not surprising given the high, daily doses administered for COVID-19 and the known propensity for this agent to prolong QTC interval, a major risk factor for drug-induced fatal arrythmias [Chorin et al2020 Heart Rhythm May 11, online ahead of print]. The substantial increase in such events relative to the standard of care in COVID-19 patients [Mehra et al., Lancet May 22, 2020, online ahead of print] is perhaps surprising, and may be because this patient population has a high incidence of comorbidities at baseline that also increase the risk of mortality and cardiac complications in COVID-19 disease. In any case, it would be beneficial to treat and prevent COVID-19 using therapeutic agents that are not cardiotoxic.

Non-clinical studies submitted as part of regulatory dossiers have shown 250-fold and 650-fold accumulation of tafenoquine in rat lung tissue relative to whole blood and plasma, respectively, and that such accumulation is the highest of any organ. See Example 2. In a practical sense, this means that even though tafenoquine was developed to target malaria parasites in the liver and blood, against which it has substantial intrinsic potency, it also has considerable utility against pathogens of the lung, against which the intrinsic potency is reduced. This is particularly so for organisms that reactivate or initiate infection by means of a non-replicative life cycle stage or spore.

In a thorough QTC study, tafenoquine at doses of up to 1200 mg over three days were not found to increase the upper limit of 90% confidence interval of the QTC interval, thereby meeting the generally accepted regulatory standard for considering a drug to not exhibit a cardiotoxicity liability [Green et al2014. J Clin Pharmacol 54:995-1005 (Green et al 2014)]. Importantly, tafenoquine also did not increase the QTC prolongation known to be associated with chloroquine when the two drugs were coadministered [Green et al 2014].

Tafenoquine, an 8-aminoquinoline, is known to effect host cell physiology in a manner different from 4-aminoquinolines such as mefloquine, chloroquine, and hydroxychloroquine, even though all four compounds are long half-life quinolines that can be used for malaria prophylaxis. For example, although mefloquine and tafenoquine, like chloroquine, both disrupt lysosomal function in mammalian cells, the effect of tafenoquine is accompanied by lipid peroxidation followed by mitochondrial dysfunction whereas this is not the case for mefloquine [Das et al 2018. Leukemia Research 70:79-86]. Furthermore, tafenoquine kills the developing liver stages and mature sexual stages of P. falciparum via site-specific two-step biochemical activation that results in local accumulation of lethal levels of hydrogen peroxide [Camarda et al 2019]. Mefloquine, chloroquine, and hydroxychloroquine do not share either this bioactivity profile or mechanism of action. It is not known which of these mechanisms predominates in mediating tafenoquine's effects on lung pathogens.

Dosing Regimens

Dosing regimens according to the invention are those that are effective in preventing and/or treating lung infection in a given subject. Administration and/or formulation are done so as to minimize gastrointestinal ("GI") upset in the subject, especially when doses 400 mg/day are given. Doses above 400 mg of tafenoquine are often not well tolerated (e.g., the dose may cause gastrointestinal issues or toxicity) by adult subjects regardless of the subjects' G6PD status. In G6PD normal adult subjects, doses of up to 400 mg of tafenoquine may be well tolerated, while in G6PD deficient subjects, doses of 300 mg or more may not be well tolerated. GI upset may be minimized and/or obviated and/or alleviated by buccal administration, sublingual administration, and/or by using a delivery design (tablet, sheet, etc.) that minimizes GI upset. Dosing may continue as necessary for up to six months provided the total dose administered does not exceed 10,800 mg in that six-month period.

In particular embodiments, the long half-life 8-aminoquinoline is tafenoquine, or a pharmaceutically acceptable salt thereof. The long half-life 8-aminoquinoline may be administered to the human subject as at least one initial (loading) dose. In particular embodiments, 100 mg-600 mg dose(s) are administered.

In further embodiments, the methods of treatment of lung infection and/or methods of prevention of lung infections, further comprising administering a second agent, such as a drug, to the human subject. In other embodiments, the method comprises administering to said subject an effective amount of a second agent. In further embodiment, the administration of tafenoquine or said compound of Formula (I) and administration of said second agent is concurrent. In yet other embodiments, the administration of tafenoquine or said compound of Formula (I) and administration of said second agent is not concurrent. In even further embodiments, no second agent is administered.

In other embodiments, the second agent is selected from the group consisting of amikacin, an aminoglycoside, amoxicillin, amphotericin formulations, any drug approved by the Food and Drug Administration for treating or preventing bacterial viral, and/or fungal infections, any azole-containing anti-fungal drug, atovaquone, azithromycin, Bactrim, bedaquiline, a benzothiazinone, BTZ043, capreomycin, cefftriaxime, cefotaxime, cefuroxamine, clindamycin, clofazimine, corticosteroids, a cyclic peptide, cycloserine, delamanid, a diarylquinoline, echinocandin, ethambutol, ethionamide, fluconazole, flucytosine, a fluoroquinolone, an imidazopyridine amide, isoniazid, itraconazole, kanamycin, levofloxacin, linezolid, a macrolide, moxifloxacin, a nitroimidazole, an oxazolidinone, PA-824, para-aminosolicyclic acid, PBTZ169, posaconazole, prothionamide, pyrazinamide, Q203, quinine, rifampin, rifapentine, SQ-109, streptomycin, sulfa drugs, sutezolid, a thioamide, trimethoprimsulfamethoxazole, vancomycin, voriconazole, any anti-viral drug, remdesivir, favipiravir, chloroquine, hydroxychloroquine, a monoclonal antibody treatment, a steroid, COVID-19 convalescent plasma, casirivimab, imdevimab, bamlanivimab, baricitinib, interleukin-6 inhibitors, kinase inhibitors, tyrosine kinsase inhibitors, Tocilizumab, ivermectin, and any combination thereof.

An embodiment of the invention is a dosing regimen according to Table 1, with or without a second agent. In particular, both methods of treatment of lung infection and methods of prevention of lung infections, the method comprises administering to said subject an effective amount of tafenoquine or a compound of Formula (I), a pharmaceutically-acceptable salt thereof, or a pharmaceutical composition comprising tafenoquine or a compound of Formula (I),

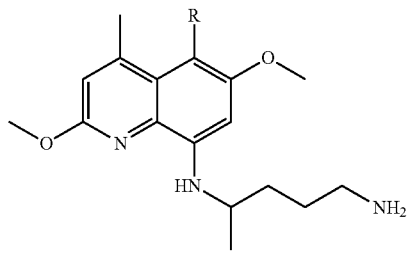

Formula (I)

wherein R is any halogen-containing substituent of molecular weight ≤205, wherein the administering is in accordance with a dosing regimen according to Table 1. For example, such a dosing regimen may be used to treat tuberculosis or Mycobacterium infections in symptomatic subjects with or without a second agent, using tafenoquine and/or long-half-life 8-aminoquinolines at the doses listed in Table 1, formulated appropriately. In another example, such a dosing regimen may be used to prevent and/or treat respiratory virus infections including SARS-CoV-2 with or without a second agent, using tafenoquine and/or long-half-life 8-aminiquinolines at the doses listed in Table 1, formulated appropriately. In yet another example, such a dosing regimen may be used to treat symptomatic Pneumocystis pneumonia, with or without a second agent, using tafenoquine and/or long-half-life 8-aminiquinolines at the doses listed in Table 1, formulated appropriately. In another example, such a dosing regimen may be used to treat fungal pneumonia caused by aspergillosis, blastomycosis, candidiasis, coccidioidomycosis, cryptococcosis, histoplasmosis, mucormycosis, Pneumocystis jirovecii pneumonia, and/or sporotrichosis in symptomatic individuals, with or without second agents, using tafenoquine or long-half-life 8-aminiquinolines at the doses at the doses listed in Table 1, formulated appropriately. In yet another example, such a dosing regimen may be used to treat pneumonia in symptomatic individuals caused by Gram positive, and other bacteria, in combination with or without a second agent, using tafenoquine or long-half-life 8-aminiquinolines at the doses at the doses listed in Table 1, formulated appropriately.

TABLE 1

| Daily dose during loading phase or during first three days of treatment (mg/day or mg/week) | | | Weekly dose for the 4th, 5th, 6th and 7th doses of treatment (mg/week) if/as required (subsequent dose(s)) | | | | Additional doses if needed (subsequent dose(s)) |
|---|---|---|---|---|---|---|---|
| Dose 1 | Dose 2 | Dose 3 | Dose 4 | Dose 5 | Dose 6 | Dose 7 | Dose 8+ |
| 400 | 400 | 400 | 400 | 400 | 400 | 400 | 400 |
| 440 | 440 | 440 | 440 | 440 | 440 | 440 | 440 |
| 480 | 480 | 480 | 480 | 480 | 480 | 480 | 480 |
| 520 | 520 | 520 | 520 | 520 | 520 | 520 | 520 |
| 560 | 560 | 560 | 560 | 560 | 560 | 560 | 560 |
| 600 | 600 | 600 | 600 | 600 | 600 | 600 | 600 |

An embodiment of the invention is a dosing regimen according to Table 2, with or without a second agent. In particular, methods of treating lung infection and methods of preventing lung infections, the method comprises administering to said subject an effective amount of tafenoquine or a compound of Formula (I), a pharmaceutically-acceptable salt thereof, or a pharmaceutical composition comprising tafenoquine or a compound of Formula (I),

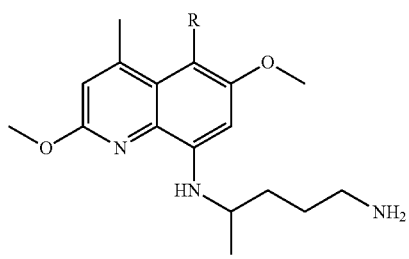

Formula (I)

wherein R is any halogen-containing substituent of molecular weight ≤205, wherein the administering is in accordance with a dosing regimen according to Table 2. For example, such a dosing regimen may be used to prevent tuberculosis and/or treat latent tuberculosis or *Mycobacterium* infections, with or without a second agent, using tafenoquine and/or long-half-life 8-aminiquinolines at the doses listed in Table 2, formulated appropriately. In another example, such a dosing regimen may be used to prevent and/or treat respiratory virus infections including SARS-CoV-2 with or without a second agent, using tafenoquine and/or long-half-life 8-aminoquinolines at the doses listed in Table 2, formulated appropriately. In yet another example, such a dosing regimen may be used to prevent *Pneumocystis* pneumonia in asymptomatic individuals at risk of contracting the disease by administering tafenoquine and/or long-half-life 8-aminiquinolines at the doses listed in Table 2, formulated appropriately. In another example, such a dosing regimen may be used to prevent and/or treat [latent] fungal pneumonia caused by aspergillosis, blastomycosis, candidiasis, coccidioidomycosis, cryptococcosis, histoplasmosis, mucormycosis, *Pneumocystis jirovecii* pneumonia, and/or sporotrichosis in asymptomatic individuals at risk of contracting the disease using tafenoquine and/or long-half-life 8-aminiquinolines at the doses listed in Table 2, formulated appropriately. In yet another example, such a dosing regimen may be used to prevent pneumonia in asymptomatic but at-risk individuals wherein the pneumonia is caused by Gram positive, and other bacteria, with or without a second agent, using tafenoquine or long-half-life 8-aminiquinolines at the doses at the doses listed in Table 2, formulated appropriately.

TABLE 2

| Daily dose during loading phase or during first three days of treatment (mg/day or mg/week)* | | | Daily or weekly dose for the 4th, 5th, 6th and 7th doses of treatment (mg/day or mg/week) if/as required, (subsequent dose(s))** | | | | Additional doses if needed (subsequent dose(s))*** |
|---|---|---|---|---|---|---|---|
| Dose 1 | Dose 2 | Dose 3 | Dose 4 | Dose 5 | Dose 6 | Dose 7 | Dose 8+ |
| 100 | 100 | 100 | 100 | 100 | 100 | 100 | 100 |
| 130 | 130 | 130 | 130 | 130 | 130 | 130 | 130 |
| 160 | 160 | 160 | 160 | 160 | 160 | 160 | 160 |
| 190 | 190 | 190 | 190 | 190 | 190 | 190 | 190 |
| 220 | 220 | 220 | 220 | 220 | 220 | 220 | 220 |
| 250 | 250 | 250 | 250 | 250 | 250 | 250 | 250 |
| 280 | 280 | 280 | 280 | 280 | 280 | 280 | 280 |
| 310 | 310 | 310 | 310 | 310 | 310 | 310 | 310 |
| 340 | 340 | 340 | 340 | 340 | 340 | 340 | 340 |
| 370 | 370 | 370 | 370 | 370 | 370 | 370 | 370 |
| 400 | 400 | 400 | 400 | 400 | 400 | 400 | 400 |
| 440 | 440 | 440 | 440 | 440 | 440 | 440 | 440 |
| 480 | 480 | 480 | 480 | 480 | 480 | 480 | 480 |

TABLE 2-continued

| Daily dose during loading phase or during first three days of treatment (mg/day or mg/week)* | | | Daily or weekly dose for the 4$^{th}$, 5$^{th}$, 6$^{th}$ and 7$^{th}$ doses of treatment (mg/day or mg/week) if/as required, (subsequent dose(s))** | | | | Additional doses if needed (subsequent dose(s))*** |
|---|---|---|---|---|---|---|---|
| Dose 1 | Dose 2 | Dose 3 | Dose 4 | Dose 5 | Dose 6 | Dose 7 | Dose 8+ |
| 520 | 520 | 520 | 520 | 520 | 520 | 520 | 520 |
| 560 | 560 | 560 | 560 | 560 | 560 | 560 | 560 |
| 600 | 600 | 600 | 600 | 600 | 600 | 600 | 600 |

*Doses ≤ 250 mg can be administered once per day for three days or once per week for three weeks. Doses > 500 mg must be administered once per week.
**Doses ≤ 250 mg can be administered once per day or once per week. Doses > 250 mg must be administered once per week. In some embodiments, no subsequent doses are administered. In other embodiments, at least one subsequent dose is administered.
***Additional doses can be administered once daily until the cumulative dose reaches 1,600 mg and must be dosed weekly thereafter.

Lung Infections:

Lung infections according to the invention may be a viral lung infection, a bacterial lung infection, a fungal lung infection, or a combination thereof. In further embodiments, said lung infection may be sensitive, resistant or multiply drug resistance to first- or second-line antimicrobials.

In other embodiments, the lung infection is tuberculosis, pneumonia, *pneumocystis* pneumonia, and/or due to Gram-positive bacteria. In another embodiment, the tuberculosis results from replicating and/or latent *Mycobacterium tuberculosis* infection. In further embodiments, the lung infection is an invasive Gram-positive bacterial infection caused by at least one bacteria selected from the list consisting of *Nocardia* spp, methicillin resistance and methicillin-sensitive *Staphylococcus aureus, Enterococcus* spp, coagulase negative *Staphylococcus*, and *Streptococcus* spp. In further embodiments, the method is for preventing or treating anthrax or other Gram positive biodefence pathogens, wherein said subject is exposed to *B. anthracis* or other relevant Gram positive bacteria.

In other embodiments, said fungal infection causes a disease selected from the group consisting of candidiasis, aspergillosis, fusariosis, cryptococcosis, trichosporonosis, mucormycosis or PCP. In further embodiments, said fungal infection is caused by at least one fungus selected from the group consisting of *Aspergillus* spp. *Candida* spp. *Fusarium* spp, *Cryptococcus* spp, *Trichosporon* spp, *Rhizopus* spp, *Mucor* spp, *Rhizomucor* spp or *Lichtheimia* spp and *Pneumocystis*. In other embodiments, the fungal infection causes disseminated candidiasis. In further embodiments the disseminated candidiasis is caused by azole-sensitive *Candida auris*, azole-resistant *C. auris*, echinochandin-sensitive *C. auris* and echinochandin-resistant *C. auris*, and/or *C. auris* resistant or sensitive to both azole and echinochandin.

In another embodiment, said lung infection is caused by a respiratory syncytial virus, para-influenza virus, rhinovirus, coronavirus and/or an influenza virus. In further embodiments, the coronavirus is any variant of human coronavirus OC43 (HCoV-OC43) (β-CoV), human coronavirus HKU1 (HCoV-HKU1) (β-CoV), human coronavirus 229E (HCoV-229E) (α-CoV), human coronavirus NL63 (HCoV-NL63) (α-CoV), Middle East respiratory syndrome-related coronavirus (MERS-CoV) (β-CoV), severe acute respiratory syndrome coronavirus (SARS-CoV) (β-CoV), or SARS-CoV-2 (β-CoV).

In particular embodiments, the lung infection is caused by a micro-organism (e.g., a bacterium, a fungus, a virus), wherein the long half-life 8-aminoquinoline (e.g., tafenoquine) exhibits a MIC of 10 μg/mL, 9 μg/mL, 8 μg/mL, 7 μg/mL, 6 μg/mL, 5 μg/mL, 4 μg/mL, 3 μg/mL, 2 μg/mL, 1 μg/mL, 0.5 μg/mL, or less against in vitro replicating said micro-organism. In particular embodiments, the long half-life 8-aminoquinoline (e.g., tafenoquine) exhibits a MIC of 5 μg/mL or less against in vitro replicating said micro-organism. In other embodiments, the long half-life 8-aminoquinoline (e.g., tafenoquine) exhibits a MIC of 4 μg/mL or less against in vitro replicating said micro-organism. In other embodiments, the long half-life 8-aminoquinoline (e.g., tafenoquine) exhibits a MIC of between 5 μg/mL and 0.5 μg/mL against in vitro replicating said micro-organism. In other embodiments, the long half-life 8-aminoquinoline (e.g., tafenoquine) exhibits a MIC of between 4 μg/mL and 0.5 μg/mL against in vitro replicating said micro-organism.

In particular embodiments, the lung infection is caused by a virus (e.g., a coronavirus), wherein the long half-life 8-aminoquinoline (e.g., tafenoquine) exhibits an EC50 or IC50 of 33 μM, 32 μM, 31 μM, 30 μM, 29 μM, 28 μM, 27 μM, 26 μM, 25 μM, 24 μM, 23 μM, 22 μM, 21 μM, 20 μM, 19 μM, 18 μM, 17 μM, 16 μM, 15 μM, 14 μM, 13 μM, 12 μM, 11 μM, 10 μM, 9 μM, 8 μM, 7 μM, 6 μM, 5 μM, 4 μM, 3 μM, 2 μM, 1 μM, 0.5 μM, or less against in vitro replicating said virus. In particular embodiments, the long half-life 8-aminoquinoline (e.g., tafenoquine) exhibits an EC50 of 20 μM or less against in vitro replicating said virus. In other embodiments, the long half-life 8-aminoquinoline (e.g., tafenoquine) exhibits an EC50 of 10 μM or less against in vitro replicating said virus. In other embodiments, the long half-life 8-aminoquinoline (e.g., tafenoquine) exhibits an EC50 of between 20 μM and 0.5 μM against in vitro replicating said virus. In other embodiments, the long half-life 8-aminoquinoline (e.g., tafenoquine) exhibits an EC50 of between 10 μM and 0.5 μM against in vitro replicating said virus.

In further embodiments said human subject, has one or more risk factors for disease progresses selected from the group consisting of: age of 60 years old or older, obesity, diabetes, and heart disease. In particular embodiments, said human subject has COVID-19 disease and has one or more risk factors for disease progresses selected from the group consisting of: age of 60 years old or older, obesity, diabetes, and heart disease. In other embodiments, the human subject with a lung infection has or is at risk of neutropenia.

The method may include detecting the presence of the bacterial, viral, and/or fungal infection prior to administration of the long half-life 8-aminoquinoline. Any suitable method for diagnosing or testing of the bacterial, viral, and/or fungal infection can be used, and such methods are well known in the art, including nucleic acid assays. In some embodiments, said subject has been confirmed to have bacterial, fungal and/or viral infection via laboratory test. In other embodiments, said subject is clinically suspected to have bacterial, fungal and/or viral infection. In additional embodiments, said bacterial, fungal, and/or viral infection includes at least one disease manifestation of infection selected from the group consisting of central nervous system, blood stream, skin, internal organ and opthalmologic involvement.

In particular embodiments, the methods of treating a lung infection and the methods of preventing a lung infection, include methods of treating and methods of preventing symptoms thereof.

In other embodiments, said subject is symptomatic of lung infection prior to administering the initial dose. In particular embodiments, the human subject is symptomatic for a bacterial, fungal, and/or viral infection (e.g., SARS-CoV-2 infection) at the time of first administration.

In other embodiments, said subject is asymptomatic of lung infection prior to the first administration. In particular embodiments, the human subject is asymptomatic for a bacterial, fungal, and/or viral infection (e.g., SARS-CoV-2 infection) at the time of first administration. In further embodiments, the human subject has tested positive for a bacterial, fungal, and/or viral infection (e.g., SARS-CoV-2 infection) at the time of the administration but is asymptomatic. In particular embodiments, the human subject is asymptomatic for the coronavirus infection and/or has been diagnosed as coronavirus negative (e.g., SARS-CoV-2 negative) at the time of the administration. In other particular embodiments, the human subject has been exposed to coronavirus (e.g., SARS-CoV-2) or has had close contact with someone infected with the coronavirus (e.g., SARS-CoV-2).

In other embodiments, said lung infection is latent prior to administering the initial dose.

In other embodiments, said subject is at risk of contracting a lung infection.

In other embodiments, the method is for preventing or treating invasive bacterial and/or fungal infections and associated morbidity and mortality in G6PD normal human subject occurring during or while in recovery from a corona viral infection (e.g., SARS-CoV-2 infection). In further embodiments, said human subject with corona viral infection has COVID-19 disease. In other embodiments, the method is for preventing or treating invasive bacterial and/or fungal infections in G6PD normal subject with suspected COVID-19 disease. In further embodiments said subject with a corona viral infection (e.g., SARS-CoV-2 infection) has or is at risk of neutropenia. In other embodiments, said subject with COVID-19 disease has or is at risk of neutropenia.

In further embodiments, said human subject has or is at risk of neutropenia. In other embodiments, said subject has or is at risk of neutropenia has hematologic malignancies. In even further embodiments said subject has or is at risk of neutropenia has received chemotherapy, is a transplant recipient under immunosuppressive treatment, is HIV positive with low T-cell counts, is experiencing other infectious diseases in which the immune system is suppressed, is taking courses of immunosuppressive medication including corticosteroids, and/or is taking antibody treatments for chronic diseases. In other embodiments, the transplant subject is receiving a bone marrow transplant, a heamatopietic stem cell transplant, or a solid organ transplant. In further embodiments, said subject has or is at risk of neutropenia, and/or is a transplant subject receiving a bone marrow transplant or a haematopoietic stem cell transplant or a solid organ transplant. In further embodiments, administration of tafenoquine to said subject comprises administration up to 90 days prior to transplantation or initiation of immunosuppressive therapy. For example, this may allow any minor hematologic changes associated with tafenoquine administration to normalize prior to transplantation or initiation of immunosuppressive therapy. In some embodiments, administration of tafenoquine comprises a dosing regimen of 200 mg/day for three days following by 200 mg once weekly for as long as permitted by regulators. In other embodiments, administration of tafenoquine comprises the dose of tafenoquine as much as 399 mg at the same regimens as described herein, or as up to 8 doses as specified in Table 1 or Table 2.

In further embodiments, said human subject has at least one of the following conditions selected from the group consisting of: is at risk of catching respiratory virus during the winter season, [and therefore of contracting secondary infections], is elderly, is a surgical subject, has a catheter or iv line, has diabetes, has obesity, has COPD, has kidney disease, and has cardiac conditions. In further embodiments the subject is a child.

EXEMPLIFIED EMBODIMENTS

Embodiment 1. A method for treating or preventing a lung infection, or a symptom thereof, in a human subject, said method comprising administering an effective amount of a long half-life 8-aminoquinoline to a subject in need thereof.

Embodiment 2. The method of embodiment 1, wherein the lung infection is caused by a bacterium, fungus, and/or virus.

Embodiment 3. The method of embodiment 1 or embodiment 2, wherein the lung infection is caused by a Gram-positive bacteria.

Embodiment 4. The method of embodiment 1 or embodiment 2, wherein the lung infection is caused by tuberculosis.

Embodiment 5. The method of embodiment 1 or embodiment 2, wherein the lung infection is a caused by a yeast, a filamentous fungi, and/or a dimorphic fungi.

Embodiment 6. The method of embodiment 1 or embodiment 2, wherein the lung infection is caused by a respiratory syncytial virus, an influenza virus, a para-influenza virus, a rhinovirus, and/or a coronaviruses.

Embodiment 7. The method of embodiment 1 or embodiment 2, wherein the lung infection is caused by a human coronavirus selected from the group consisting of HCoV-0043, HCoV-HKU1, HCoV-229E, HCoV-NL63, SARS-CoV-2, SARS-CoV, MERS-CoV, and any variant thereof.

Embodiment 8. The method of embodiment 1 or embodiment 2, wherein the lung infection is an invasive bacterial and/or fungal infection, and wherein the subject has COVID-19 or is recovering from a coronavirus infection.

Embodiment 9. The method of embodiment 1 or embodiment 2, wherein the lung infection is *Pneumocystis* pneumonia.

Embodiment 10. The method of embodiment 1 or embodiment 2, wherein the lung infection is tuberculosis.

Embodiment 11. The method of embodiment 1 or embodiment 2, wherein the lung infection is caused by *Staphylococcus aureus, Streptococcus pneumoniae, Enterococcus faecalis, Enterococcus faecium*, and/or *Mycobacterium tuberculosis*.

Embodiment 12. The method of embodiment 1 or embodiment 2, wherein the lung infection is caused by *Aspergillus* spp. *Candida* spp. *Fusarium* spp, *Cryptococcus* spp, *Trichosporon* spp, *Rhizopus* spp, *Mucor* spp, *Rhizomucor* spp or *Lichtheimia* spp, *Pneumocystis*, azole-sensitive *Candida auris*, azole-resistant *C. auris*, echinochandin-sensitive *C. auris*, echinochandin-resistant *C. auris*, and/or *C. auris* resistant or sensitive to both azole and echinochandin.

Embodiment 13. The method of embodiment 1 or embodiment 2, wherein the lung infection is caused by at least one micro-organism selected from the list consisting of a respiratory syncytial virus, an influenza virus, a parainfluenza virus, a rhinovirus, HCoV-OC43, HCoV-HKU1, HCoV-229E, HCoV-NL63, SARS-CoV-2, SARS-CoV, MERS-CoV, *Staphylococcus aureus, Streptococcus pneumoniae, Enterococcus faecalis, Enterococcus faecium*, and/or *Mycobacterium tuberculosis, Aspergillus* spp. *Candida* spp. *Fusarium* spp, *Cryptococcus* spp, *Trichosporon* spp, *Rhizopus* spp, *Mucor* spp, *Rhizomucor* spp or *Lichtheimia* spp, *Pneumocystis*, azole-sensitive *Candida auris*, azole-resistant *C. auris*, echinochandin-sensitive *C. auris*, echinochandin-resistant *C. auris*, and/or *C. auris* resistant or sensitive to both azole and echinochandin, and any variant thereof.

Embodiment 14. The method according to any one of the preceding embodiments, wherein the lung infection is caused by a micro-organism, wherein the long half-life 8-aminoquinoline is capable of inhibiting said micro-organism in vitro at a minimum inhibitory concentration ("MIC") of 10 µg/mL or less, 9 µg/mL or less, 8 µg/mL or less, 7 µg/mL or less, 6 µg/mL or less, 5 µg/mL or less, 4 µg/mL or less, 3 µg/mL or less, 2 µg/mL or less, or 1 µg/mL or less.

Embodiment 15. The method of any preceding embodiment, wherein the long half-life 8-aminoquinoline is tafenoquine or a pharmaceutically acceptable salt thereof.

Embodiment 16. The method of any preceding embodiment, wherein the subject has the lung infection at the time of said administering.

Embodiment 17. The method of any preceding embodiment, wherein prior to or contemporaneously with said administering, identifying the subject as having the lung infection and/or identifying the subject as having a bacterial, fungal, and/or viral infection.

Embodiment 18. The method of embodiment 17, wherein said identifying comprises assaying a biological sample (e.g., blood, saliva, urine, nasal secretion) obtained from the subject for the presence of a micro-organism nucleic acid or protein.

Embodiment 19. The method of embodiment 18, wherein said assaying comprises use of reverse transcriptase-polymerase chain reaction (RT-PCR), immunological assay (e.g., ELISA), or Plaque-reduction neutralization testing (PRNT).

Embodiment 20. The method according to any one of embodiments 1 to 15, wherein the subject does not have a lung infection at the time of administering, and wherein the long half-life 8-aminoquinoline is administered as prophylaxis.

Embodiment 21. The method according to any one of the preceding embodiments, wherein tafenoquine or the long half-life 8-aminoquinoline is administered orally, intravascularly, nasally, rectally, parenterally, subcutaneously, or intramuscularly.

Embodiment 22. The method of embodiment 21, wherein tafenoquine or the long half-life 8-aminoquinoline is administered orally or said administering is via sub lingual and/or buccal route(s).

Embodiment 23. The method according to any preceding embodiment, further comprising administering a second agent for treating or preventing a bacterial, fungal, and/or viral infection, or a symptom thereof, in the same formulation as the long half-life 8-aminoquinoline, or in a separate formulation before, during, or after administering the long half-life 8-aminoquinoline.

Embodiment 24. The method according to embodiment 23, wherein the second agent is selected from the group consisting of amikacin, an aminoglycoside, amoxicillin, amphotericin formulations, any drug approved by the Food and Drug Administration for treating or preventing bacterial viral, and/or fungal infections, any azole-containing antifungal drug, atovaquone, azithromycin, Bactrim, bedaquiline, a benzothiazinone, BTZ043, capreomycin, cefftriaxime, cefotaxime, cefuroxamine, clindamycin, clofazimine, corticosteroids, a cyclic peptide, cycloserine, delamanid, a diarylquinoline, echinocandin, ethambutol, ethionamide, fluconazole, flucytosine, a fluoroquinolone, an imidazopyridine amide, isoniazid, itraconazole, kanamycin, levofloxacin, linezolid, a macrolide, moxifloxacin, a nitroimidazole, an oxazolidinone, PA-824, para-aminosolicyclic acid, PBTZ169, posaconazole, prothionamide, pyrazinamide, Q203, quinine, rifampin, rifapentine, SQ-109, streptomycin, sulfa drugs, sutezolid, a thioamide, trimethoprimsulfamethoxazole, vancomycin, voriconazole, any anti-viral drug, remdesivir, favipiravir, chloroquine, hydroxychloroquine, a monoclonal antibody treatment, a steroid, COVID-19 convalescent plasma, casirivimab, imdevimab, bamlanivimab, baricitinib, interleukin-6 inhibitors, kinase inhibitors, tyrosine kinsase inhibitors, Tocilizumab, ivermectin, and any combination thereof.

Embodiment 25. The method according to any one of embodiments 1 to 22, wherein no second agent is administered before administering an initial dose of tafenoquine or the long half-life 8-aminoquinoline.

Embodiment 26. The method according to any one of embodiments 1 to 22, wherein no second agent is administered during administering an initial dose of tafenoquine or the long half-life 8-aminoquinoline.

Embodiment 27. The method according to any one of embodiments 1 to 22, wherein no second agent is administered after administering an initial dose of tafenoquine or the long half-life 8-aminoquinoline.

Embodiment 28. The method according to any preceding embodiment, wherein the subject is at risk or has at least one condition selected from the group consisting of age of 60 years old or older, obesity, diabetes, heart disease, neutropenia, hematologic malignancies, chemotherapy, transplant recipient under immunosuppressive treatment, HIV positive with low T-cell counts, other infectious diseases in which the immune system is suppressed, taking courses of immunosuppressive medication including corticosteroids, taking antibody treatments for chronic diseases, receiving a bone marrow transplant, receiving a heamatopietic stem cell transplant, receiving a solid organ transplant, catching respiratory virus during the winter season, a surgical subject, has a catheter or iv line, COPD, kidney disease, and/or cardiac conditions.

Embodiment 29. The method according to embodiment 28, wherein said subject is a transplant recipient or receiving immunosuppressive treatment, wherein said administering is 90 days or less prior to transplantation or initiation of immunosuppressive therapy.

Embodiment 30: The method according to any one of the preceding embodiments, wherein the subject is glucose-6-phosphate dehydrogenase (G6PD)-normal.

Embodiment 31: The method according to any one of the preceding embodiments, wherein said administering is conducted according to the dosing regimen of any one of Table 1 and Table 2 and/or according to any of the Examples.

Embodiment 32: The method according to any one of embodiments 1 to 14, wherein the method is for treating or for preventing a lung infection, wherein said administering comprises:

(a) administering to said subject an effective amount of tafenoquine or a compound of Formula (I), a pharmaceutically-acceptable salt thereof, or a pharmaceutical composition comprising tafenoquine or a compound of Formula (I), and

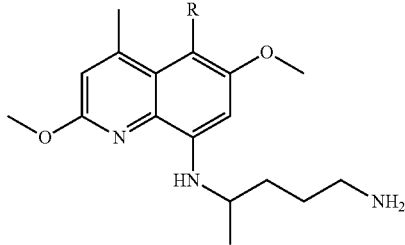

Formula (I)

wherein R is any halogen-containing substituent of molecular weight ≤205.

Embodiment 33. The method according to embodiment 32, wherein said subject is G6PD-normal.

Embodiment 34. The method according to embodiment 32 or 33, wherein at least seven doses of about 100 mg-600 mg of Formula (I) are administered.

Embodiment 35. The method according to any one of embodiments 32 to 34, wherein no more than 10,800 mg is administered to said subject in a six-month period.

Embodiment 36. The method according to any one of embodiments 32 to 35, wherein the measured half-life of the compound of Formula (I) is at least three times greater than the measured half-life of primaquine.

Embodiment 37. The method according to any one of embodiments 32 to 35, wherein the measured half-life or its metabolites in plasma or lung is at least three times longer than the measured half-life of primaquine in plasma or lung.

Embodiment 38. The method according to any one of embodiments 32 to 35, wherein said compound of Formula (I) is an 8-aminoquinoline with a measured half-life greater than primaquine.

Embodiment 39. The method according to any one of embodiments 32 to 35, wherein the measured half-life of the 8-aminoquinoline or its metabolites in plasma or lung is longer than the measured half-life of primaquine in plasma or lung.

Embodiment 40. The method according to any one of embodiments 32 to 39, wherein about 100 to about 600 mg of said compound of Formula (I) is administered in one or more initial dose(s).

Embodiment 41. The method according to any one of embodiments 32 to 40, wherein about 100 to about 600 mg of said compound of Formula (I) is administered in one or more initial dose(s) and in one or more subsequent dose(s).

Embodiment 42. The method according to any one of embodiments 32 to 41, wherein three initial doses are administered once per day for three days.

Embodiment 43. The method according to any one of embodiments 32 to 41, wherein three or four initial doses are administered.

Embodiment 44. The method according to any one of embodiments 41 to 43, wherein the subsequence dose(s) is administered once per week.

Embodiment 45. The method according to any one of embodiments 41 to 43, wherein the subsequence dose(s) is administered once per day.

Embodiment 46. The method according to any one of embodiments 40 to 44, wherein the initial dose(s) is about 200 mg.

Embodiment 47. The method according to any one of embodiments 40 to 44, wherein the initial dose(s) is about 150 mg.

Embodiment 48. The method according to any one of embodiments 40 to 45, wherein the initial dose(s) is about 100 mg.

Embodiment 49. The method according to any one of embodiments 41 to 48, wherein the subsequent dose(s) is about 200 mg.

Embodiment 50. The method according to any one of embodiments 41 to 48, wherein the subsequent dose(s) is about 150 mg.

Embodiment 51. The method according to any one of embodiments 41 to 48, wherein the subsequent dose(s) is about 100 mg.

Embodiment 52. The method according to any one of embodiments 41 to 51, wherein the first subsequent dose is administered seven days after the last initial dose.

Embodiment 53. The method according to any one of embodiments 32 to 41, wherein an initial doses is about 200 mg and is administered once a day for three days, and wherein a subsequent dose is about 200 mg and is administered once a week.

Embodiment 54. The method according to any one of embodiments 40, 42, 43, 46, 47, or 48, wherein there are no subsequent doses.

Embodiment 55. The method according to any embodiment of 32 to 41, wherein administering is 200 mg on Day 1, 200 mg on Day 2 [+/−1 day], 200 mg on Day 3 [+/−1 day], and 200 mg on Day 10 [+/− one day], and no further doses are administered.

Embodiment 56. The method according to any of the preceding embodiments, wherein the lung infection is caused by a virus, wherein the long half-life 8-aminoquinoline is capable of inhibiting said virus in in vitro cell culture with a 50% effective concentration ["EC50"] or a 50% inhibitory concentration ["IC50"] of 33 μM or less, 32 μM or less, 31 μM or less, 30 μM or less, 29 μM or less, 28 μM or less, 27 μM or less, 26 μM or less, 25 μM or less, or 24 μM, or less, 23 μM, or less, 22 μM, 21 less, 20 μM or less, 19 μM or less, 18 μM or less, 17 μM or less, 16 μM or less, 15 μM or less, 14 μM or less, 13 μM or less, 12 μM or less, or 11 μM, or less, 10 μM, or less, 9 μM, or less, 8 μM or less, 7 μM or less, 6 μM or less, 5 μM or less, 4 μM or less, 3 μM or less, 2 μM or less, or 1 μM or less.

Embodiment 57. The method according to any of the preceding embodiments, wherein the lung infection is caused by a virus, wherein the long half-life 8-aminoquinoline is tafenoquine and is capable of inhibiting said virus in in vitro cell culture with a 50% effective concentration ["EC50"] or a 50% inhibitory concentration ["IC50"] of 33 μM or less, 32 μM or less, 31 μM or less, 30 μM or less, 29 μM or less, 28 μM or less, 27 μM or less, 26 μM or less, 25 μM or less, or 24 μM, or less, 23 μM, or less, 22 μM, 21 less, 20 μM or less, 19 μM or less, 18 μM or less, 17 μM or less, 16 μM or less, 15 μM or less, 14 μM or less, 13 μM or less, 12 μM or less, or 11 μM, or less, 10 μM, or less, 9 μM, or less, 8 μM or less, 7 μM or less, 6 μM or less, 5 μM or less, 4 μM or less, 3 μM or less, 2 μM or less, or 1 μM or less.

Embodiment 58: The method according to any one of the preceding embodiments, wherein said administering is con-

EXAMPLES

Figure 2:
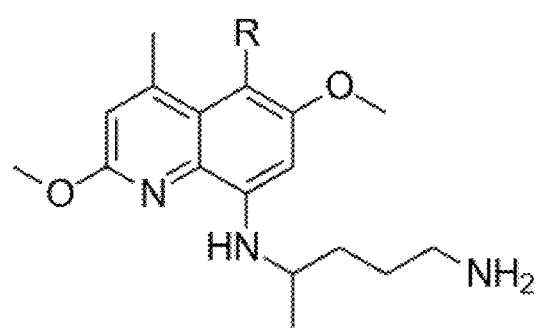

Example 1—Substituted 8-Aminoquinolines are More Active and have Broader Spectrum of Activity than Primaquine Tafenoquine is more potent and has a broader spectrum of activity against malaria parasites and *Pneumocystis* in vivo as a consequence of its longer half-life (14 days versus approximately 6 hours). This occurs as a consequence of substitutions at the 2, 4, and 5 positions that increase steric bulk, lipophilicity, and block sites of metabolic attack. Tafenoquine and similarly substituted 8-aminoquinolines such as those illustrated in FIG. 1A and FIG. 2 exhibit more potent and broader spectrums of action against lung pathogens and lung diseases of humans and animals in a manner similar to what is described in the examples for tafenoquine.

Figure 3:
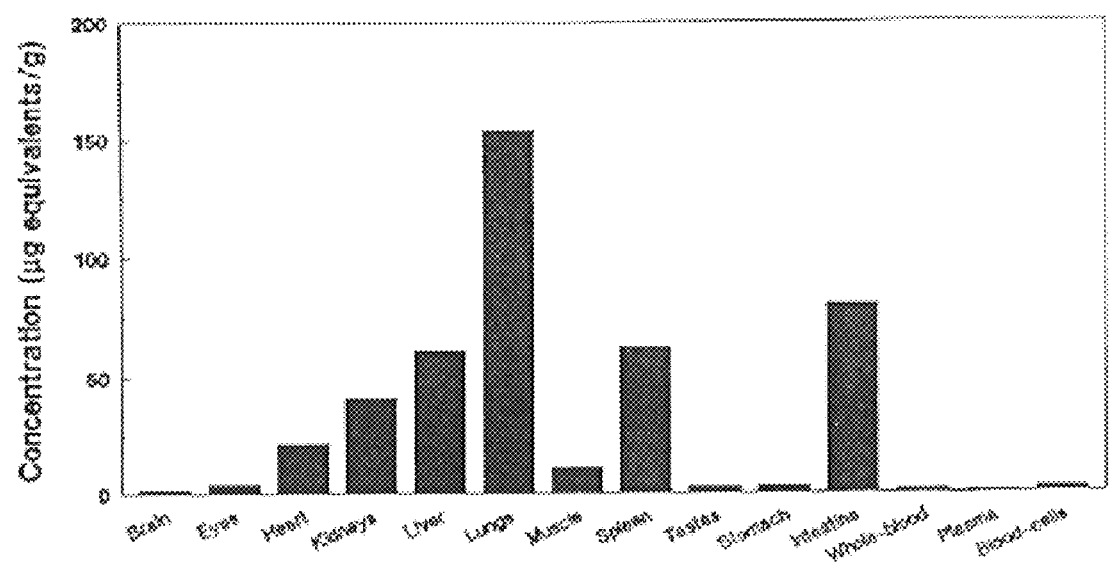

Example 2—Tafenoquine Accumulates 250-Fold and 650-Fold in the Lung Relative to Whole Blood and Plasma in Rats In this study, a single oral dose of [14C]radio-labeled tafenoquine (25 mg base/kg) was given to 60 male rats, and then groups of 5 animals were killed at time points ranging from 30 minutes to 120 hours post-dose. Radioactivity in the combusted organs of killed animals was measured by liquid scintillation analysis. When expressed as microgram equivalents tafenoquine per gram of tissue, the concentration of tafenoquine in lung were at 0.5, 1, 6, 12, 24, 48, 72, 96, and 120 hours post-administration were 1.21, 6.43, 133, 154, 136, 119, 83.7, 59.4, and 44.4, respectively. The lung:blood concentration ratio was found to be 250. In separate partitioning experiments the ratio of the blood cell:plasma concentration was found to be approximately 2.6, meaning that the approximate ratio of lung:plasma concentrations in this species is 650. Tafenoquine was found to accumulate in lung more than any other tissue in the body, as shown in FIG. 3. In separate partitioning experiments the ratio of the blood cell: plasma concentration was found to be 1.4 for humans.

Example 3— Minimum Inhibitory Concentrations of Tafenoquine In Vitro Against *Pneumocystis*

Bartlett et al., 1991 established that a concentration of tafenoquine [WR238605] of 10 microgram/ml was required to decrease parasitemia in vitro from baseline, whereas lower concentrations suppressed parasitemia but did not decrease parasitemia relative to baseline. Therefore, the minimum inhibitory concentration in vitro is approximately 10 microgram/ml.

Example 4—Steady State Versus Single Dose Plasma Levels of Tafenoquine in Humans PK simulations of the approved prophylactic dose for malaria in humans indicates that the Cmax following a single dose is approximately 90 nanogram/ml whereas the steady state Cmax is 300 nanogram/ml [see FIG. 1 of Dow and Smith, 2017, Malaria Journal 16:209]. Therefore, the ratio between steady state and single dose concentrations is approximately 3.3 [300 ng/ml divided by 90 ng/ml, then rounded down]. [Note: These calculated values provided in this example were recalculated and updated in the present application and therefore may differ from what is presented in some cross-referenced U.S. Provisional Applications.]

Example 5—Minimum Inhibitory Concentrations of Tafenoquine In Vivo Against *Pneumocystis*

Queener et al. 1992. Efficacy of intermittent dosage of 8-aminoquinolines for therapy or prophylaxis of *Pneumocystis* pneumonia in rats. J Infect Dis 165:764-768 (Queener et al 1992) and Bartlett et al., 1991 demonstrated that the minimum dose of tafenoquine required to reduce parasitemia nearly to zero was 4 mg/kg administered once every 4 days orally and 4 mg/kg/day daily orally for prophylaxis and treatment respectively (over a two to three week period). Given the duration of these studies one can assume that drug levels were at steady state. Assuming dosing parity between the labeling study and these in vivo studies with *Pneumocystis*, and steady state drug levels 3.3-fold higher in rats as is the case in humans, one can deduce that the effective minimum inhibitory concentrations ("MICs") in lungs for treatment and prophylaxis are 81 [4 mg/kg/day divided by 25 mg/kg multiplied by 154 ug/g and 3.3=81.3 which was rounded down to 81] and 23 micrograms/g [total dose of 16 mg/kg over 14 days=1.14 mg/kg/day divided by 25 mg/kg multiplied by 154 ug/g and 3.3=23.2 which was rounded down to 23], respectively. These correspond with steady state plasma levels of approximately 125 [81.3 ug/ml*1000/650, then rounded up to 125] and 36 nanogram/ml [23.2 ug/ml*1000/650, rounded up to 36].

Thus, the MICs in vivo for treatment and prophylaxis of *Pneumocystis* are approximately 8.1 and 2.3-fold higher than the MIC in vitro, which is approximately 10 ug/ml as reported by Bartlett et al. 1991 and Queener et al. 1992 [Note: These calculated values provided in this example were recalculated and updated in the present application and therefore may differ from what is presented in some cross-referenced U.S. Provisional Applications.]

Example 6— Doses of Tafenoquine Effective for Prophylaxis and Treatment of *Pneumocystis* in Humans A loading dose of tafenoquine administered over three days of 600 mg (200 mg once per day for three days for a total of 600 mg) followed by 200 mg administered once per week for a minimum of two weeks generates steady state concentrations above 80 nanogram/ml in 95% of individuals (this represents a total of five doses of 200 mg, or a total dose of 1000 mg, to achieve steady state concentrations above 80 nanogram/ml in 95% of individuals). This dose may be administered over 5 weeks (i.e., 200 mg once per week for 5 weeks) or over 5 days (i.e., 200 mg per day for 5 days) to achieve the same steady state concentration.

The pharmacokinetics of tafenoquine are proportional with the dose administered in the therapeutic range.

A minimum of two weeks of exposure to steady state drug levels is required for efficacious prophylaxis or treatment. Thus, a minimum of seven doses may be required to achieve treatment or prophylactic efficacy.

Therefore, for treatment of *Pneumocystis* it may be necessary to administer seven doses of about 313 mg [125 ng/ml divided by 80 ng/ml multiplied by a dose of 200 mg, then rounded up]. This could be achieved by administration once per week for seven weeks or as a 939 mg load over three days followed by administration of 313 mg once per week for 4 weeks.

Therefore, for prophylaxis of *Pneumocystis*, it may be necessary to administer at least seven doses of about 90 mg [36 ng/ml divided by 80 ng/ml multiplied by a dose of 200 mg], once per day for seven days, once per week for seven weeks, or as a about 270 mg load followed by about 90 mg once per week for 4 weeks to achieve minimum state plasma levels of >36 nanogram/ml for at least two weeks. [Note: These calculated values provided in this example were recalculated and updated in the present application and therefore may differ from what is presented in some cross-referenced U.S. Provisional Applications.]

Example 7—Tafenoquine is More Potent than Primaquine In Vitro Against *P. falciparum*

The average 50% inhibitory concentrations of tafenoquine and primaquine against seven different strains of *P. falciparum* were determined from three repeat in vitro assays [Vennerstrom et al. 8-aminoquinolines active against blood stage *Plasmodium falciparum* in vitro inhibit haematin polymerization. Antimicrobial Agents and Chemotherapy. 1999; 43:598-60]. Tafenoquine was on average 7.1-fold more potent than primaquine.

Example 8—In Vitro Activity of Primaquine Against Replicating *Mycobacterium tuberculosis*

Rajic et al. 2018. Molecules 2018, 23, 1724 (Rajic et al. 2018) observed that primaquine exhibited an MIC of 256 microgram/ml against replicating *Mycobacterium tuberculosis* in vitro.

Example 9—In Vitro and Ex Vivo Activity of Tafenoquine Against *Mycobacterium tuberculosis*

Tafenoquine (as its succinate salt) is anticipated to be active with an MIC <100 micrograms/ml or 150 microM (i.e., greater than 7-fold more potent than primaquine) against replicating *Mycobacterium tuberculosis* in in vitro assays as well as in ex vivo macrophage assays using standard screening assays intended for this purpose (e.g., using assay systems similar to or as described by Oh et al. 2018. J. Med. Chem. 2018, 61, 9952-9965 (Oh et al. 2018)).

Example 10—Tafenoquine is More Active Against Quiescent Versus Actively Dividing *Plasmodium Cynomolgi*

In the relapsing *Plasmodium cynomolgi*-Rhesus macacque model, the dose of tafenoquine required to eliminate the replicating blood stage forms of the parasite (6 mg/kg/day for three days) is 10-fold higher than the dose required to kill the quiescent hypnozoites [(0.6 mg/kg/day for three days), see Dow et al., 2011 Radical curative efficacy of tafenoquine combination regimens in *Plasmodium cynomolgi*-infected *Rhesus monkeys* (Macaca mulatta), MALARIA JOURNAL, 10:212].

Example 11—In Vitro Activity of Tafenoquine Against Non-Replicating *Mycobacterium tuberculosis*

Tafenoquine (as its succinate salt), as is the case with non-replicating versus replicating malaria, is anticipated to be 10-fold more potent against non-replicating *Mycobacterium tuberculosis* in vitro with an MIC of 10 micrograms/ml under non-replicating/anaerobic conditions (e.g., using assay systems similar to or as described by Wayne et al. An in vitro model for sequential study of shiftdown of *Mycobacterium tuberculosis* through two stages of nonreplicating persistence. Infect. Immun. 1996, 64, 2062-2069; Boshoff et al. Biosynthesis and recycling of nicotinamide cofactors in *Mycobacterium tuberculosis* an essential role for NAD in nonreplicating bacilli. J. Biol. Chem. 2008, 283, 19329-19341; and Oh et al. 2018).

Example 12—Doses Required for Treatment and Prophylactic Efficacy of Tafenoquine Against Tuberculosis in Humans Since the in vitro MIC of *Pneumocystis* is 10 micrograms/ml and the MIC against non-replicating tuberculosis is anticipated to be10 micrograms/ml one would expect the effective doses to eliminate non-replicating tuberculosis to be approximately the same. To achieve the desired MIC in the lungs, a minimum steady state plasma concentration of 36 nanogram/ml would need to be maintained to prevent the development of symptomatic tuberculosis in asymptomatic individuals. Therefore, for tafenoquine monotherapy, efficacy would be achieved following administration of at least seven doses of 90 mg, administered according to one of the following four ways: (1) once per day for seven days; (2) once per week for seven weeks; (3) as a 270 mg load (90 mg once per day for three days for a total dose of 270 mg) followed by 90 mg once per week for 4 weeks; or (4) administering the total 630 mg dose over two to three days, provided that no more than 600 mg are administered on any of those three days. Any of the preceding dosing strategies will achieve the required minimum steady state plasma levels of >36 nanogram/ml for at least two weeks.

Since the MIC of tafenoquine against replicating forms of tuberculosis [Examples 19-22] in vitro were 4.7-18 ug/ml, and the MIC of tafenoquine against *Pneumocystis* is 10 ug/ml, if follows that for treatment of tuberculosis, the target steady state plasma concentration would be 59 [4.7/10*125 ng/ml, rounded up] to 225 ng/ml [18/10*125 ng/ml]. Tafenoquine is anticipated to have utility against replicating tuberculosis in humans following administration of at least seven doses of 148 [59 ng/ml/80 ng/ml*200 mg, rounded up]-563 mg [225 ng/ml/80 ng/ml*200 mg, rounded up]. This may be achieved by administration according to one of the following ways: (1) administering 148-563 mg of tafenoquine once per week for seven weeks; or (2) administering 148-563 mg of tafenoquine per day for three days (for a total loading dose of 444-1689 mg) followed by administration of 148-563 mg once per week for 4 weeks. Where daily doses >400 mg are required, tafenoquine may be administered in an alternate formulation to minimize GI adverse events. Tafenoquine may be administered in combination with other drugs where it can be shown that doing so further reduces the MIC. [Note: These calculated values provided in this example were recalculated and updated in the present application and therefore may differ from what is presented in some cross-referenced U.S. Provisional Applications.]

Example 13—Prevention of Gram-Positive Bacterial Pneumonia in Humans Using Tafenoquine Gram-positive micro-organisms contributing to community, hospital, and ventilator-acquired pneumonia include *Staphylococcus aureus* [Ferreira-Coimbra et al, 2019; Shioshin et al. 2020]. A priori administration of 8-aminoquinolines can prevent the occurrence of such pneumonia and associated morbidity and mortality in the at-risk population.

Primaquine is active in vitro against *Staphylococcus aureus* with an MIC of 50 microgram/ml [Rajic et al. 2018] and has broader activity against other pneumonia-associated lung pathogens.

Tafenoquine is anticipated to have activity against bacterial pathogens causing pneumonia in the 16-20 microgram/ml range in vitro and anticipated to be effective for prevention following the administration of at least seven doses of 100-600 mg with doses in excess of 400 mg alternatively formulated to prevent GI disturbances.

Example 14—Treatment of Gram-Positive Bacterial Pneumonia in Humans Using Tafenoquine Gram-positive micro-organisms contributing to community, hospital, and ventilator-acquired pneumonia include *Staphylococcus aureus* [Ferreira-Coimbra et al, 2019; Shioshin et al. 2020]. Treatment of such pneumonia with 8-aminoquinolines in combination with existing antimicrobials improves the cure rate of such infections and thereby decreases morbidity and mortality Tafenoquine may be administered in an alternate formulation to minimize GI events and in combination with other antibiotics if MICs in vitro can be reduced to <10 microgram/ml. Tafenoquine is anticipated to have utility in treating pathogen-acquired pneumonia in humans following administration of seven doses of 400-600 milligrams in an appropriate formulation to limit GI disturbances. This may be achieved by administration once per week for seven weeks or as a load over three days followed by administration of once per week for 4 weeks.

Example 15—Doses of Tafenoquine Effective for Prophylaxis and Treatment of Pneumonia-Causing Fungi in Humans Immunosuppressed individuals are at greater risk of contracting pneumonia caused by inhalation of non-replicating spores of *Aspergillus, Sporothrix, Mucormycetes, Blastomyces, Coccidia* spp, *Cryptococcus neoformans, Cryptococcus gatti*, and *Histoplasma*.

Doses of tafenoquine and other long half-life 8-aminoquinolines effective for prevention of such infections are anticipated to be up to seven-fold lower than those required for the prevention of *Pneumocystis*, due to the mode of transmission being via a non-replicating spore. Therefore, it may be necessary to administer a course of at least seven doses of 20 to 600 mg, appropriately spaced on a daily or weekly basis, with the total dose never exceeding 1800 mg over three days (i.e., never exceeding 600 mg once per day for three days). If the total cumulative dose was required to be greater than 1800 mg, the 8-aminoquinoline may be administered at a dose of ≤600 mg per week, or at a dose of ≤per week following an ≤1800 mg load (the load being ≤600 mg every day for three days for a total loading dose of ≤1800 mg), or as appropriate. In the instances described above in this paragraph, tafenoquine or the 8-aminoquinoline would need to be appropriately formulated to minimize GI effects if given at daily doses of >400 mg. And, as with the regimens described in Table 1 and Table 2, each dose would have the same milligram strength whether it is administered daily or weekly.

For treatment of such fungal infections it would be necessary to administer seven doses, each >400 mg. This may be achieved by administration once per week for seven weeks or as a 1200 mg load over three days followed by administration of 400 mg once per week for 4 weeks. This is achievable using formulations that minimize gastrointestinal disturbance since this drug-related adverse event limits the currently achievable dose using traditional tablet technology to a maximum daily dose of 400 mg.

Example 16—Activity of 8-Aminoquinolines Against Viral Lung Infections

Tafenoquine is anticipated to inhibit the replication of lung viruses such as influenza and corona viruses in vivo at well tolerated doses and in vitro in cellular assay systems using metabolically competent lung cells. Lung viruses may be exquisitely sensitive to 8-aminoquinolines due to their proximity to higher levels of 8-aminoquinolines in the lungs, and the capacity of lung tissue to undergo Phase I and other metabolic reactions.

The exquisite selectivity of primaquine to sexual blood stage parasites is thought to be mediated via a two-step host-mediated activation whereby (i) primaquine is converted to quinonimine metabolites by cytochrome P450 activity then (ii) reduction of the quinonimine metabolites by cP450 NADPH oxidoreductase by bone marrow [Camarda et al 2019]. The second reaction leads to local accumulation of hydrogen peroxide. It has been proposed [Camarda et al 2019] that the sequestration of gametocytes in bone marrow exposes them to locally high levels of hydrogen peroxide leading to selective killing of the parasite stage (primaquine has little effect against the blood stages of *P. falciparum* which do not sequester in bone marrow).

Analogously 8-aminoquinolines are proposed to generate elevated levels of hydrogen peroxide levels in the lung due to the presence of both cytochrome P450 enzymes and cytochrome P-450 NADPH oxidoreductases [Hall et al., 10(3) CARCINOGENESIS 521-530 (March 1989); Anttila S. et al. Cytochrome P450-mediated pulmonary metabolism of carcinogens: regulation and cross-talk in lung carcinogenesis. Am J Respir Cell Mal Biol. 2011 May; 44(5):583-9]. Co-location of intracellular viral replication with elevated hydrogen peroxide levels in lung tissue is anticipated to lead to reduced viral replication in the presence of 8-aminoquinolines. To exhibit clinical utility (treatment or prophylaxis) against a corona virus infection it would be necessary to administer at least one 100 mg dose of tafenoquine or an 8-aminoquinoline and perhaps up to seven or more doses as per the dosing regimens required for other lung infections (see Table 1 and Table 2).

Example 17—Tafenoquine is Active Against Medically Important Yeasts, Dimorphic Fungi, and Filamentous Fungi The activity of tafenoquine was evaluated in vitro against a panel of medically important yeasts, dimorphic fungi, and filamentous fungi as described below.

Preparation and Storage of Investigational Agents—Stock solutions of the investigational agents were prepared at concentrations 100-times the highest concentration to be tested (6400 µg/ml) using dimethyl sulfoxide. Aliquots of the stock solutions were dispensed into polypropylene vials and stored at −20° C.

Growth Medium and Dilution of Investigational Antifungal Agents—The synthetic medium RPMI-1640 (with glutamine, without bicarbonate, and with phenol red) was used. The RPMI was buffered to a pH of 7.0±0.1 at 25° C. with 0.165M MOPS (3-[N-morpholino] propanesulfonic acid). Sterile U-shaped 96-well cell culture plates were used for performing the MIC assays. Dilutions of the DMSO stocks were prepared into RPMI to achieve 2×concentrations. After the dilutions of the working 2×investigational antifungal solutions were prepared, 0.1 ml of each concentration was transferred into a pre-specified column of the U-shaped 96-well cell culture plate using sterile pipettes.

Inoculum Preparation—Fungal isolates were grown on Sabouraud dextrose agar (yeasts) or potato flake agar (filamentous fungi) and cells were collected after an appropriate period of growth for each species being evaluated (e.g., 48-72 hours for yeasts and 7 days for filamentous fungi). The fungi were suspended in sterile distilled water, and the densities of the fungal suspension were read using a spectrophotometer and adjusted to an appropriate optical density specific for each fungal species. The fungal suspension of each isolate was then diluted in RPMI. A sufficient volume of the test inoculum was prepared to directly inoculate 0.1 ml into each test well of the 96-well cell culture plate. Final inoculum ranges are dependent on the fungal species to be tested (e.g., $0.4 \times 10^3$ to $5 \times 10^3$ cells/ml for yeasts and dimorphic fungi, and $0.4 \times 10^4$ to $5 \times 10^4$ cells/ml for filamentous fungi). Each well of the 96-well cell culture plate containing the investigational antifungal compounds (0.1 ml volume) was inoculated on the day of the assay with 0.1 ml of the fungal suspension. Growth control wells contained 0.1 ml of fungal suspension and 0.1 ml of the growth medium without antifungal agents. The media control well contained 0.2 ml of the growth medium.

Incubation and Reading of MIC Results—The microdilution trays were incubated at 35° C. without agitation. After the appropriate period of incubation (24 hours for *Candida* and the Mucorales, 48 hours will be used for *Aspergillus*, the dematiaceous fungi, *Fusarium*, and *Sporothrix*, 72 hours for *Cryptococcus*, and Scedosporium, 48-72 hours for *Coccidioides, Blastomyces*, and Emergomyces, and 168 hours for *Histoplasma*) the trays and microdilution tubes were removed and the MIC values determined. Two MIC values were assigned to each investigational agent: 1) the concentration resulting in a prominent reduction in growth (50% inhibition compared to the growth control), and 2) the concentration resulting in complete inhibition of growth (100% inhibition vs. growth control). One positive comparator/control was used for yeast (fluconazole) and one will be used for filamentous fungi (posaconazole or voriconazole). These comparators represent agents from each of the available antifungal classes that are first line therapies for subjects with infections caused by these fungi. For each batch of investigational agents prepared we also evaluated the activities of available antifungal agents against appropriate quality control and reference strains of fungi (i.e., *C. parapsilosis* ATCC 20219, *C. krusei* ATCC 6258, and *P. variotii* MYA-3630).

Susceptibility Data— Tafenoquine exhibited MICs of 2-32 ug/ml against all the fungal species evaluated. Tafenoquine was active against all fungal species evaluated with MICS<=32 microg/ml [Tables 3 and 4].

TABLE 3

Susceptibility of yeasts to tafenoquine

| Species | Isolate No. | Tafenoquine Succinate 50% | Tafenoquine Succinate 100% | Fluconazole 50% |
|---|---|---|---|---|
| *C.parapsilosis* | ATCC 22019 | 4 | 4 | 1 |
| *C. krusei* | ATCC 6258 | 4 | 4 | 32 |
| *Candida albicans* | SC5314 | 8 | 8 | 0.5 |
| | ATCC 90028 | 4 | 4 | 0.25 |
| | CA3 | 4 | 4 | >64 |
| *Candida auris* | DI17-47 | 4 | 4 | >64 |
| | DI17-48 | 2 | 4 | 2 |
| | DI17-46 | 4 | 4 | >64 |
| *Candida glabrata* | 05-62 | 8 | 8 | >64 |
| | 05-761 | 8 | 8 | 8 |
| | CG3 | 8 | 8 | 32 |
| *Candida guilliermondii* | Cgui1 | 2 | 4 | 1 |
| | Cgui2 | 2 | 2 | 2 |
| | Cgui3 | 4 | 4 | 2 |
| *Candida parapsilosis* | CP1 | 4 | 4 | 0.5 |
| | CP2 | 4 | 4 | 0.5 |
| | CP3 | 4 | 8 | 0.5 |
| *Cryptococcus neoformans* | USC1597 | 4 | 4 | 4 |
| | H99 | 4 | 4 | 16 |
| | CN3 | 4 | 4 | 64 |

TABLE 4

Susceptibility of filamentous fungi and dimorphic fungi to tafenoquine
FILAMENTOUS & DIMORPHIC FUNGI (Microdilution & Macrodilution)

| Species | Isolate No. | Tafenoquine Succinate 50% | Tafenoquine Succinate 100% | Posaconazole 100% | Voriconazole 100% | Fluconazole 50% |
|---|---|---|---|---|---|---|
| *P. variotii* | MYA-3630 | 4 | 4 | ≤0.03 | 0.125 | 8 |
| *Rhizopus arrhizus* | 99-880 | 4 | 4 | 1 | — | — |
| | 99-892 | 4 | 4 | 0.25 | — | — |
| | RAI | 8 | 16 | 0.125 | — | — |
| *Sporothrix* sp. | Sporo1 | 2 | 4 | 0.06 | — | — |
| | Sporo2 | 1 | 2 | 1 | — | — |
| | Sporo3 | 2 | 4 | 0.06 | — | — |
| *Apophysomyces* sp. | Apo1 | 8 | 8 | 0.06 | — | — |
| | Apo2 | 2 | 4 | ≤0.03 | — | — |
| | Apo3 | 16 | 32 | 0.5 | — | — |
| *Saksenaea* sp. | Sak1 | 4 | 8 | ≤0.03 | — | — |
| | Sak2 | 2 | 2 | 0.06 | — | — |
| | Sak3 | 8 | 8 | ≤0.03 | — | — |
| *Aspergillus flavus* | ATCC 204304 | 4 | 4 | — | 1 | — |
| | Aflav2 | 8 | 16 | — | 2 | — |
| | Aflav3 | 4 | 8 | — | 1 | — |

TABLE 4-continued

Susceptibility of filamentous fungi and dimorphic fungi to tafenoquine
FILAMENTOUS & DIMORPHIC FUNGI (Microdilution & Macrodilution)

| Species | Isolate No. | Tafenoquine Succinate 50% | Tafenoquine Succinate 100% | Posaconazole 100% | Voriconazole 100% | Fluconazole 50% |
|---|---|---|---|---|---|---|
| Aspergillus fumigatus | AF293 | 8 | 16 | — | 1 | — |
|  | D115-106 | 4 | 8 | — | >16 | — |
|  | D115-116 | 4 | 4 | — | 8 | — |
| Fusarium sp. | FSI | 8 | 16 | — | 8 | — |
|  | FO1 | 8 | 16 | — | 4 | — |
|  | FS2 | 16 | 16 | — | >16 | — |
| Altenaria sp. | Alt1 | 2 | 4 | — | 2 | — |
| Curvularia sp. | Curv1 | 2 | 8 | — | 0.5 | — |
| Exserohilum sp. | Exser1 | 4 | 8 | — | 0.5 | — |
| Scedosporium sp. | 00-180 | 4 | 8 | — | — | 0.125 |
|  | LPI | 4 | 8 | — | — | 4 |
|  | Scedo1 | 4 | 4 | — | — | 0.125 |
| Blastomyces dermatitidis | Blasto1 | 1 | 2 | — | — | ≤0.03 |
|  | Blasto2 | 4 | 4 | — | — | ≤0.03 |
|  | Blasto3 | 8 | 8 | — | — | ≤0.03 |
| Emergomyces sp. | Emerg2 | 4 | 4 | — | — | ≤0.03 |
|  | Emerg3 | 2 | 4 | — | — | ≤0.03 |
| Histoplasma capsulatum | HC1 | 4 | 4 | — | — | 0.125 |
|  | HC2 | 2 | 4 | — | — | ≤0.03 |
|  | HC3 | 8 | 8 | — | — | ≤0.03 |
| Coccidioides sp. | Cocci1 | 4 | 8 | — | — | 16 |
|  | Cocci2 | 16 | 16 | — | — | 32 |
|  | D117-143 | 16 | 16 | — | — | 4 |

Example 18—Tafenoquine is Active Against *Staphylococcus aureus*, *Streptococcus Pneumoniae*, *Enterococcus Faecalis* and *Enterococcus faecium*

The activity of tafenoquine was evaluated in vitro against a panel of medically important bacteria by determining the MIC using broth microdilution testing as described below.

Growth Medium—Cation adjusted Mueller-Hinton broth was used as the test medium. Broth for panel preparation was prepared from commercial dehydrated medium (Difco formulation, BD Diagnostics, catalog number 275730). The medium was hydrated according to the manufacturer's instructions, and the cation content was adjusted as needed to achieve the recommended 20-25 mg/L calcium and magnesium 10-12.5 mg/L. For Streptococci the broth was supplemented with 3% lysed horse blood.

Dilution of Investigational Agents—Polystyrene test tubes were used to prepare the drug dilutions and sterile U-shaped 96-well polystyrene microtiter trays were used for performing the MIC assays. Stock solutions of the investigational agents were prepared at concentrations 100-times the highest concentration to be tested (6400-1.25 μg/ml) using dimethyl sulfoxide. Aliquots of the stock solutions were dispensed into polypropylene vials and stored at −20° C. Further dilutions (1:50) were made in the culture medium (cation-adjusted Mueller-Hinton medium).

After the dilutions of the working 2-fold investigational antibacterial solutions were prepared, 50 μL of each concentration was transferred into rows of the first 10 wells of each 12-well column of the U-shaped disposable 96-well microtiter trays using a multichannel pipettor. The 11$^{th}$ well in each row served as the sterility control, and the 12th well contained only culture medium to serve as the growth control for each isolate. In like manner, the control drug for the organism being tested was prepared in a separate 96 well panel exactly as described above. A 50 μL volume of the standardized inoculum suspension of each test isolate was prepared in culture medium to directly inoculate each test well of the drug containing microtiter tray.

Inoculum Preparation—Colonies of each strain generated on sheep blood agar plates with overnight growth at 35° C. in ambient air were used to directly prepare a suspension equivalent in density to the 0.5 McFarland opacity standard.

The exact turbidity of each suspension was determined using a desktop portable photometer. For panels containing 2×drug concentrations, a 1:100 dilution of the McFarland organism suspension was prepared in cation-adjusted Mueller-Hinton broth and 50 μL aliquots of each test (and control) strain was added to each well of the designated rows of the microtiter trays using a multichannel pipettor. The target inoculum concentration was 5×10$^5$ CFU/ml in each well.

Incubation and Reading of MIC Results—The microdilution trays were incubated at 35° C. in ambient air for 16-20 hours (5% $CO_2$ for Streptococci). Trays were removed and each well were inspected for evidence of growth (turbidity). The MIC was defined as the lowest concentration of the investigational agent and the control drug that prevents visibly discernible growth in the test wells. In order for a test to be considered acceptable, the growth control had to demonstrate good growth of the isolate, the sterility control had to remain clear, and the MIC of the control drug had to in the acceptable range for the relevant control organism.

Susceptibility Data— Tafenoquine exhibited an MIC of 8 microg/ml against *Staphylococcus aureus*, *Enterococcus faecalis* and *Enterococcus faecium* and an MIC of 16 ug/ml against *Streptococcus pneumoniae* [Table 5].

TABLE 5

Susceptibility of selected bacterial strains to tafenoquine

| Isolate # | Organism ID | Date Tested | MIC (µg/ml) Vancomycin | MIC (µg/ml) Meropenem | MIC (µg/ml) ARAKODA (tafenoquine) |
|---|---|---|---|---|---|
| ATCC 29213 | S. aureus | Sep. 10, 2020 | 1 | — | 8 |
| 6215 | S. aureus | Sep. 10, 2020 | 1 | — | 8 |
| 6229 | S. aureus | Sep. 10, 2020 | 1 | — | 8 |
| ATCC 29212 | E. faecalis | Sep. 10, 2020 | 2 | — | 8 |
| 1593 | E. faecium | Sep. 10, 2020 | >64 | — | 8 |
| 1768 | E. faecalis | Sep. 10, 2020 | 16 | — | 8 |
| ATCC 49619 | S. pneumoniae | Sep. 10, 2020 | ≤0.125 | — | 16 |
| MD77773 | S. pneumoniae | Sep. 10, 2020 | 0.25 | — | 16 |
| CO314937 | S. pneumoniae | Sep. 10, 2020 | ≤0.125 | — | 16 |
| ATCC 25922 | E. coli | Sep. 10, 2020 | — | ≤0.125 | >64 |
| J4243 (MO72) | E. coli | Sep. 10, 2020 | — | ≤0.125 | >64 |
| J4244 (JJ1886) | E. coli | Sep. 10, 2020 | — | ≤0.125 | >64 |
| ATCC 17978 | A. baumannii | Sep. 10, 2020 | — | ≤0.125 | 64 |
| AR-88 | A. baumannii | Sep. 10, 2020 | — | >64 | 64 |
| AR-273 | A. baumannii | Sep. 10, 2020 | — | 64 | >64 |
| ATCC 27853 | P. aeruginosa | Sep. 10, 2020 | — | 0.25 | >64 |
| AR-230 | P. aeruginosa | Sep. 10, 2020 | — | >64 | >64 |
| J4242 | P. aeruginosa | Sep. 10, 2020 | — | 8 | >64 |
| ATCC 70063 | K. pneumoniae | Sep. 10, 2020 | — | ≤0.125 | >64 |
| AR-97 | K. pneumoniae | Sep. 10, 2020 | — | 64 | >64 |
| AR-113 | K. pneumoniae | Sep. 10, 2020 | — | >64 | >64 |

S. pneumoniae tested in CA-MHB with 3% LHB

Example 19—Efficacy of Tafenoquine Against *M. tuberculosis* in Standard 7H9 Media Containing Casitone The minimum inhibitory concentration [MIC] of tafenoquine against *M. tuberculosis* [ATCC #27294] was determined in clear round bottom 96 [8×12 Nunclon polystyrene] plates as follows. 50 ul/well of the desired test medium was added to all wells except the first column [of 8 wells]. Drug diluted in the intended medium containing no more than 1% dimethylsulfoxide (DMSO) at twice the intended final concentration was added to the first column in the desired row [50 ul/well]. Using a multichannel pipettor, 504 was transferred to each column starting with column 1 and ending with column 12 [50 uL was discarded after column 12]. Prior to the MIC assay, isolated *M. tuberculosis* cells were grown in the desired media until an optical density of 0.2 to 0.3 was reached and were then diluted 1:1000 in the same medium and 50 uL containing approximately $1 \times 10^4$ bacteria per well was added to each well of the 96 well plate. Plates were incubated for a total of 2 weeks inside zip-lock bags placed in a 37° C. incubator with room air. Each drug concentration was tested in a single well on two independent plates. Isoniazid and DMSO [0.5%] were used as positive and negative controls. Concentration ranges of tafenoquine and isoniazid tested were 25-0.104 microg/ml and 50-0.024 microM, respectively. At weeks 1 and 2, plates were read qualitatively with an inverted enlarging mirror plate reader and graded qualitatively as either growth or no growth. The MIC was the higher of [i] the lowest concentration completely inhibiting growth or [ii] the average of the lowest concentration completely inhibiting growth and the next lowest concentration if partial growth was observed at that lower concentration.

The media used for the MIC studies consisted of the following components: 1000 mL double distilled water, 4.7 g Middlebrook 7H9 broth powder, 0.5 ml tyloxapol added with a sterile syringe, 4 g glucose, 0.81 g NaCL, 0.3 g of Bacto Casitone (Difco). The mixtures stirred until dissolved then filter sterilized with 0.2 micron filter.

MICs of tafenoquine at 1 and 2 weeks were 4.7 and 6.25 ug/ml, respectively, as outlined in Table 12. MICs of isoniazid at 1 and 2 weeks were 0.1 and 0.15 microM, respectively.

TABLE 6

MICs of tafenoquine and isoniazid under various conditions

| Conditions/Drugs | MICs in µg/ml for tafenoquine and microM for isoniazid under various conditions | | | | | | | |
|---|---|---|---|---|---|---|---|---|
| Duration of Exposure | 1 week | 2 weeks | 1 week | 2 weeks | 1 week | 2 weeks | 1 week | 2 weeks |
| Glucose | X | X | X | X | | | | |
| Casitone | X | X | | | X | X | | |
| BSA | | | X | X | | | X | X |
| DPPC | | | | X | X | X | X | X |
| Cholesterol | | | | | | | X | X |
| Tafenoquine | 4.7 | 6.25 | 12.5 | 19 | 4.7 | 6.25 | 9.4 | 12.5 |
| Isoniazid | 0.1 | 0.15 | 0.2 | 0.3 | 0.07 | 0.1 | 0.2 | 0.3 |

Example 20—Activity of Tafenoquine Against *M. tuberculosis* in 7H9 Media Containing Glucose and Bovine Serum Albumin In order to assess whether protein binding influenced the activity of tafenoquine, casitone was replaced with bovine serum albumin ("BSA"). MICs were determined as described in Example 19, except that the media used was prepared as follows:

To 1000 mL of double distilled water was added 4.7 g 7H9 broth powder, 5 g BSA fraction V, 0.81 g NaCl, 0.5 ml tyloxapol from a sterile syringe and 4 g glucose. The media was stirred and filter sterilized using a 0.2 micron filter.

The MICs of tafenoquine and isoniazid were determined as described in Example 19 and were at 1 and 2 weeks were 12.5/19 microg/ml and 0.2/0.3 microM, respectively [Table 6].

Example 21—Activity of Tafenoquine Against *M. tuberculosis* in 7H9 Media Containing DPPC and Casitone In order to assess whether an alternate carbon source, prevalent in the lung, influenced the activity of tafenoquine, glucose in the base medium was replaced with DPPC, which is the most prominent lipid in the lung. MICs were determined as described in Example 19, except that the media used was prepared as follows:

To 1000 mL of double distilled water was added 4.7 g 7H9 broth powder, 0.3 g Bacto Casitone (Difco), 0.81 g NaCl, 0.5 ml tyloxapol from a sterile syringe and 1 ml of a 14 mg/ml solution of DPPC (previously prepared by dissolving 70 mg DPPC in 5 ml of ethanol and vortexing, then filter sterilizing to make a 14 mg/ml solution). The media was stirred and filter sterilized using a 0.2 micron filter.

The MICs of tafenoquine and isoniazid were determined as described in Example 19 and were at 1 and 2 weeks were 4.7/6.25 microg/ml and 0.07/0.1 microM, respectively [see Table 6].

Example 22—Activity of Tafenoquine Against *M. tuberculosis* in 7H9 Media Containing DPPC, Cholesterol and BSA In order to assess the combined effect of protein binding and another alternative carbon source on the activity of tafenoquine, DPPC was replaced with DPPC/cholesterol and casitone was replaced with BSA in the culture medium as described below. Cholesterol was tested because it accumulates in granulomas.

To 1000 mL of double distilled water was added 4.7 g 7H9 broth powder, 0.81 g NaCl, 5 g of BSA fraction V, 0.5 ml of a 10 mg/ml solution of DPPC (previously prepared as described in Example 21 but at a different concentration), and 1.5 ml of a stock solution of 16 mg/ml cholesterol solution in a 1:2 mixture of tyloxapol/ethanol (prepared by adding 1 ml ethanol to 0.5 ml of tyloxapol in a 15 ml plastic tube, microwaving for 1-2 min in 30s intervals, then adding 24 mg cholesterol, and heating as before until the mixture is dissolved and uniform). The media was filter sterilized a 0.2 micron filter.

The MICs of tafenoquine and isoniazid were determined as described in Example 19 and were at 1 and 2 weeks were 9.4/12.5 ug/ml and 0.2/0.3 microM, respectively [see Table 6].

Example 23—Primaquine does not Exhibit Antiviral Activity In Vitro

Primaquine was found by Rajic et al 2018 to exhibit no antiviral activity [EC 50>50 microM] against a panel of viruses consisting of Para-Influenza-3 virus, Reovirus, Sindbis virus, Cocsackie B4 virus, Punto Toro virus and Yellow Fever Virus [Rajic et al 2018].

Example 24—Tafenoquine Inhibits COVID-19 Replication In Vitro

In vitro susceptibility of viruses to an antiviral agent may be assessed using a quantitative assay to measure virus replication in the presence of increasing concentrations of the product compared to replication in the absence of the product. The effective concentration is the concentration of product at which virus replication is inhibited by 50 percent (EC50 for cell-based assays). Assays that evaluate antiviral activity include, but are not limited to, virus inactivation assays, plaque reduction assays, cytopathic effect inhibition assays, peripheral blood mononuclear cell (PBMC) assays, and binding and fusion assays [FDA Guidance for Industry, Antiviral Product Development—Conducting and Submitting Virology Studies to the Agency. U.S. Department of Health and Human Services, Food and Drug Administration, Center for Drug Evaluation and Research (CDER). June 2006].

4 Day Assay:

The in vitro susceptibility of SARS-CoV-2 to tafenoquine was first assessed in a 4-day cytopathic effect ("CPE") inhibition assay and then is being assessed in a 2-day TCID-50 assay.

Briefly, for the 4-day CPE assay, Vero E6 cells were seeded into 96-well plates at $2 \times 10^4$ cells/well in 100 μL seeding media (Minimal Essential Medium supplemented with 1% (w/v) L-glutamine, 2% fetal bovine serum). Plates were incubated overnight at 37° C., 5% $CO_2$.

A 9-point, 3-fold dilution series was initially prepared in DMSO (25,000 uM-3.8 uM) followed by transfer of a volume of each compound dilution into virus growth media (Minimal Essential Medium supplemented with 1% (w/v) L-glutamine, 2% FBS, 4 μg/mL TPCK-Trypsin). Each tafenoquine intermediate dilution series was added to the pre-seeded Vero E6 plates so that the final concentration range was 50 uM-7.6 nM.

SARS-CoV-2 diluted in virus growth media to generate a moi of 0.05, was added to the 96-well plates. This moi was previously determined to provide 100% CPE in 4 days. Virus was added to triplicate rows to assess viral activity and virus growth media without virus was added to triplicate rows to assess cytotoxicity. Plates were incubated at 37° C., 5% $CO_2$ for 4 days prior to staining with MTT.

After incubation for four days, viable cells were determined by staining with MTT. A solution of MTT was added to plates (final concentration 1 mg/mL) and incubated for 2 hours at 37° C. in a 5% $CO_2$ incubator. Wells were aspirated to dryness and formazan crystals solubilised by the addition of 2-Propanol. Absorbance was measured at 540-650 nm on a plate reader. The percent cell protection achieved by the positive control and test articles in virus-infected cells was calculated by the formula of Pauwels et al Rapid and automated tetrazolium-based colorimetric assay for the detection of anti-HIV compounds. J Virol Methods. 1988 August; 20(4):309-21 and the $EC_{50}$ values were calculated via non-linear regression.

The 50% cytotoxic concentration ($CC_{50}$) was defined as the concentration of the test compound that reduced the absorbance of the mock infected cells by 50% of the control value.

Remdesivir and hydroxychloroquine were used as positive controls.

Tafenoquine exhibited an EC50 of 15.7 microM, a CC50 of 37.2 microM, with a selectivity index of 2.4. Remdesivir exhibited at EC50 of 0.7 uM, a CC50 of >100 uM, and a selectivity index of >143 uM. Hydroxychloroquine exhibited 43% inhibition at the highest non-toxic concentration [33 microM], meaning that an EC50 could not be calculated. The CC50 of hydroxychloroquine was approximately 55 microM.

The difference in EC50 between remdesivir and tafenoquine may be because remdesivir is a direct antiviral, whereas tafenoquine alters host cell physiology that offers a mechanism of viral replication different or complementary to other quinolines.

48 Hour Assay:

The reduction in virus titre after exposure to tafenoquine for a 48-hour period was assessed via Tissue Culture Infective Dose 50 ("TCID50").

A 5-point, 3-fold dilution series of Tafenoquine (50 uM-0.6 uM) was prepared in assay media and added to Vero E6 cells, pre-seeded overnight in 24 well plates. SARS-CoV-2 was diluted in virus growth media to generate a moi of 0.05 and was added to the 24-well plates and plates incubated for 48 hours. The remaining virus was quantified via TCID50 assay. Plates were incubated for three days at 37° C. in a humidified 5% CO2 atmosphere, and virus-induced CPE scored visually. The TCID50 of the virus suspension was determined using the method of Reed L J, Muench H. A simple method of estimating fifty percent endpoints. Am J Hyg. 1938; 27:493-7.

Hydroxychloroquine was used as a positive control.

Tafenoquine exhibited an EC50 of 2.6 microM. The selectivity index, calculated relative to the CC50 of 37.2 microM for the 4-day test, was 14.3. Hydroxychloroquine exhibited an EC50 of 10.4 microM. The selectivity index, calculated relative to the CC50 of 67 microM for the 4-day test, was 5.3.

The increased potency and selectivity of tafenoquine in the 48 h assay compared to the 96 h assay is presumably because the number of replication cycles in the 48 h assay are fewer.

These data demonstrate that tafenoquine has intrinsic activity against SARS-CoV-2 that may provide clinical benefit, and exhibits much greater potency and selectivity than hydroxychloroquine.

Example 25: Tafenoquine Exhibits Surprising Antiviral Activity Against SARS-CoV-2 in Human Respiratory Cells and is More Active than Other Quinoline Antimalarials Hydroxychloroquine and chloroquine are active against SARS-CoV-2 in VERO cells but do not exhibit antiviral effect in animals. Moreover, randomized clinical trials of hydroxychloroquine and chloroquine do not support substantial clinical benefit in humans [Rosenke et al Hydroxychloroquine Proves Ineffective in Hamsters and Macaques Infected with SARS-CoV-2. bioRxiv. June 2020; Skipper et al Hydroxychloroquine in Nonhospitalized Adults With Early COVID-19: A Randomized Trial. Ann Intern Med. July 2020; Wang et al Remdesivir and chloroquine effectively inhibit the recently emerged novel coronavirus (2019-nCoV) in vitro. Cell Res. 2020; 30(3):269-271; Hoffman et al Chloroquine does not inhibit infection of human lung cells with SARS-CoV-2. Nature (2020) (Hoffman et al., 2020)] demonstrated that chloroquine and hydroxychloroquine were 10-fold less potent in the epithelial cell line CALU-3 than in VERO cells and in VERO cells expressing the protease TRMPSS2. Since SARS-CoV-2 is considered to enter human respiratory cells via a TRMPSS2-mediated mechanism rather than the low endosomal pH-dependent dependent mechanism important for entry into VERO cells, the clinical failure of hydroxychloroquine has been attributed to its inability to inhibit only the pH-dependent entry mechanism which is not present in human respiratory epithelial cells [because it acts by increasing host cell endosomal pH, see Hoffman et al 2020]. It has become dogma in the field that all quinoline antimalarials act in the same way and, thus, that all quinoline antimalarials will not work in epithelial cells or provide clinical benefit.

In vitro susceptibility data were generated for tafenoquine in the human endothelial cell line CALU3. As described herein, it was surprisingly found, especially given the literature, that tafenoquine exhibits useful inhibition of antiviral replication at pharmacologically achievable concentrations.

Figure 4:
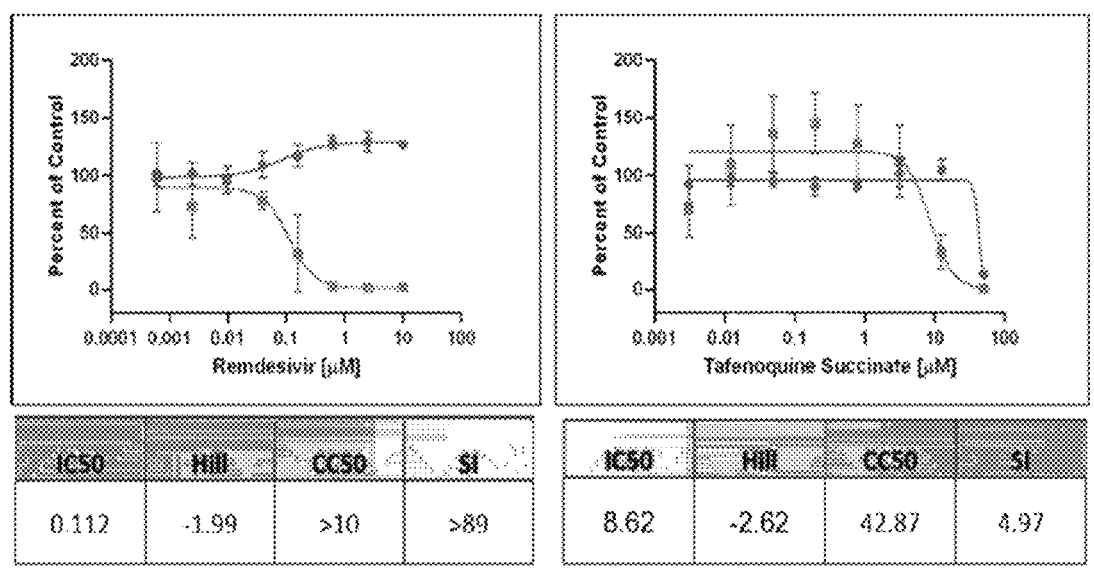

The EC50 of [same as the IC50 referred to in FIG. 4] tafenoquine against SARS-CoV-2 in CALU-3 cells was determined as described briefly in FIG. 4 and in detail as described by Dittmar et al., Drug repurposing screens reveal FDA approved drugs active against SARS-Cov-2. bioRxiv. June 2020 (Dittmar et al., 2020), and found to be 8.6 microM. The raw data are in FIG. 5. The cell culture medium used included 10% fetal bovine serum. Results showed that tafenoquine was more potent than any other quinoline antimalarial screened by Dittmar et al., 2020 in CALU3 cells.

Example 26: Tafenoquine is Likely to Exhibit Useful Antiviral Activity Against SARS-CoV-2 in Humans at Relevant Therapeutic Doses

*Pneumocystis* was used as a model organism against which to set minimum requirements for the maximum acceptable in vitro EC50 of tafenoquine against SARS-CoV-2 in vitro. *Pneumocystis* was selected because it is the only lung pathogen for which both in vitro and in vivo data are available for tafenoquine. The maximum lung tissue concentration [$LT_{sscmaxrats}$] at the minimum dose of tafenoquine necessary to inhibit the growth of *Pneumocystis* in vivo in a treatment modality was calculated using relevant data derived from the scientific literature [see Table 7]. The ratio of that concentration to the EC50 against *Pneumocystis* in vitro $R_{LTEC}$ was determined [see Table 7]. The plasma steady state Cmax [$P_{sscmaxhuman}$] at the approved prophylactic dose is known from the ARAKODA product insert [60 Degrees Pharmaceuticals. 2018. Product Insert for ARAKODA.]. The maximum steady state lung tissue concentration [$LT_{sscmaxhumans}$] of that dose was determined using relevant metrics from the literature. The maximum permissible EC50 ("MPEC50") was then defined by dividing the $LT_{sscmaxhumans}$ by the $R_{LTEC}$ [Table 7].

As can be seen from Table 7, the ratio of the $R_{LTEC}$ to the EC50 of tafenoquine against *Pneumocystis* was determined to be 23. The steady state Cmax at the approved prophylactic dose is known based on prior modeling. The maximum steady state lung tissue concentration of that dose was estimated to be 389 microM [Table 7]. The maximum permissible EC50 ("MPEC50") was then defined by dividing the maximum steady state lung tissue concentration by the LTPI which is 16.7 microM.

Since the measured EC50 of tafenoquine in human respiratory cells is lower than 16.7 microM, it can be concluded that therapeutically relevant doses of tafenoquine should exhibit useful therapeutic efficacy against SARS-CoV-2 in humans.

Since the minimum dose required to exhibit a statistically significant effect on *Pneumocystis* replication in vivo in a treatment modality is 1 mg/kg every 4 days compared to 2 mg/kg every 4 days for treatment, it follows that the MPEC50 of tafenoquine for prevention of SARS-CoV-2 must be two-fold higher [33.4 microM]. Since the actual EC50 against SARS-CoV-2 is lower than this, it follows that the approved dose for malaria prophylaxis in humans should also exhibit useful prophylactic efficacy against SARS-CoV-2. [Note: These calculated values provided in this example were recalculated and updated in the present application and therefore may differ from what is presented in some cross-referenced U.S. Provisional Applications.]

TABLE 7

Calculation of $R_{LTEC}$ and MPEC50 for tafenoquine against SARS-CoV-2

| Parameter | Value | Source/Assumptions |
| --- | --- | --- |
| Dose in female rats required to exhibit a statistically significant impairment of Pneumocystis replication in a treatment modality | 2 mpk q 4 days | From Bartlett et al 1991 and Queener et al 1992. Assumed to be a steady state dosing regimen approximately equivalent to weekly dosing in humans. Note that the equivalent dose that exhibited a statistically significant effect on Pneumocystis replication in vivo in a prophylactic modality was 1 mpk q 4 days. This is also referenced in the narrative description for Example 26. |
| Maximum plasma concentration following a single 125 mpk dose in female rats | 2240 ng/ml | Dow et al 2017 Tafenoquine is not neurotoxic following supertherapeutic dosing in rats. Travel Med Infect Dis 17:18-24 |
| Estimate of plasma concentration following a single dose of 2 mpk in rats | 35.84 ng/ml | Assumes linearity of Cmax with dose from 2 to 125 mpk [2/125*2240] |
| Ratio of whole blood to plasma concentration [rat] | 2.6 | Example 2 |
| Ratio of lung to whole blood concentration [rat] | 250 | Example 2 |

TABLE 7-continued

Calculation of $R_{LTEC}$ and MPEC50 for tafenoquine against SARS-CoV-2

| Parameter | Value | Source/Assumptions |
| --- | --- | --- |
| $LT_{cmaxrats}$ | 23,296 ng/ml | Multiply plasma Cmax by 2.6 and 250 |
| Approximate EC50 of tafenoquine against Pneumocystis in vitro | 1 microg/ml | From Bartlett 1991 |
| $R_{LTEC}$ | 23.3 | Divide steady state Cmax by EC50 [23,296/1000/1, round up] |
| Ratio of whole blood to plasma concentration [human] | 1.4 | Example 2 |
| Ratio of lung to whole blood concentration for humans assumed to be the same as rats | 250 | Example 2 |
| $P_{sscmaxhumans}$ | 646.8 ng/ml | From Section 12 of the ARAKODA product insert. Multiply Cmax of a single dose of 200 mg by 4.4 to get the steady state Cmax at the approved human dose for malaria prophylaxis [147 ng/ml *4.4]. |
| $LT_{sscmaxhumans}$ | 389 microM | Multiply human median steady state plasma concentration by 1.4, then 250, the convert from ng/ml to microM [647 × 1.4 × 250/581.6, then round down] |
| MPEC50 | 16.7 microM | Divide steady state lung Cmax by $R_{LTEC}$ |

Example 27: Tafenoquine does not Exhibit Antiviral Activity Against Cytomegaloviruses In Vitro Human foreskin fibroblast (HFF) cells prepared from human foreskin tissue were obtained from the University of Alabama at Birmingham tissue procurement facility with approval from its IRB. The tissue was incubated at 4° C. for 4 h in Clinical Medium consisting of minimum essential media (MEM) with Earl's salts supplemented with 10% fetal bovine serum (FBS) (Hyclone, Inc. Logan Utah), L-glutamine, fungizone, and vancomycin. Tissue is then placed in phosphate buffered saline (PBS), minced, rinsed to remove the red blood cells, and resuspended in trypsin/EDTA solution. The tissue suspension is incubated at 37° C. and gently agitated to disperse the cells, which are collected by centrifugation. Cells are resuspended in 4 ml Clinical Medium and placed in a 25 $cm^2$ flask and incubated at 37° C. in a humidified $CO_2$ incubator for 24 h. The media is then replaced with fresh Clinical Medium and the cell growth is monitored daily until a confluent monolayer has formed. The HFF cells are then expanded through serial passages in standard growth medium of MEM with Earl's salts supplemented with 10% FBS, L-glutamine, penicillin, and gentamycin. The cells are passaged routinely and used for assays at or below passage 10 (Hartline et al., Antiviral Res. 2018. A standardized approach to the evaluation of antivirals against DNA viruses: Orthopox-, adeno-, and herpesviruses. November; 159:104-112 (Hartline et al. 2018); Prichard et al., Activity and mechanism of action of N-methanocarbathymidine against herpesvirus and orthopoxvirus infections. Antimicrob Agents Chemother. 2006; 50(4):1336-41). COS7, C-33 A, Guinea Pig Lung, and Mouse embryo fibroblast cells were obtained from ATCC and maintained in standard growth medium of MEM with Earl's salts supplemented with 10% FBS, L-glutamine, penicillin, and gentamycin.

Akata cells were kindly provided by John Sixbey (Louisiana State University, Baton Rouge, La.). BCBL-1 cells were obtained through the NIH AIDS Research and Reference Reagent Program, Division of AIDS, NIAID, NIH. Molt-3 cells were obtained from Scott Schmid at the Centers for Disease Control and Prevention, Atlanta, Ga. Lymphocytes are maintained routinely in RPMI 1640 (Mediatech, Inc., Herndon, Va.) with 10% FBS, L-glutamine and antibiotics and passaged twice a week, as described previously (Keith et al., Antiviral Res. 2018. A standardized approach to the evaluation of antivirals against DNA viruses: Polyomaviruses and lymphotropic herpesviruses. November; 159: 122-129; Prichard et al., Benzimidazole analogs inhibit human herpesvirus 6. Antimicrob Agents Chemother. 2011; 55(5):2442-5).

The E-377 strain of HSV-1 was a gift of Jack Hill (Burroughs Wellcome). The HCMV strain AD169, HSV-2 strain G, AdV5 strain Adenoid 75, GPCMV strain 22122 and MCMV strain Smith were obtained from the American Type Culture Collection (ATCC, Manassas, Va.). The Copenhagen strain of VACV and Brighton strain, CPXV were kindly provided by John W. Huggins (Department of Viral Therapeutics, Virology Division, United States Army Medical Research Institute of Infections Disease). VZV, strain Ellen, the BK virus Gardner strain and JC virus MAD4 strain were obtained from the ATCC. Akata cells latently infected with EBV were obtained from John Sixbey. The Z29 strain of HHV-6B was a gift of Scott Schmid at the Centers for Disease Control and Prevention, Atlanta Ga. HHV-8 was obtained as latently infected BCBL-1 cells through the NIH AIDS Research and Reference Reagent Program.

Each experiment that evaluates the antiviral activity of the compounds includes both positive and negative control compounds to ensure the performance of each assay. Concurrent assessment of cytotoxicity is also performed for each study in the same cell line and with the same compound exposure (see below).

CPE assays for HCMV, MCMV, and GPCMV were performed in monolayers as described (Hartline et al. 2018). Briefly, cells were seeded in 384 well plates and incubated for 24 h to allow the formation of confluent monolayers. Dilutions of test drug were prepared directly in the plates and the monolayers infected at a predetermined MOI based on virus used. After incubation, cytopathology was determined by the addition of CellTiter-Glo (CTG) reagent. Concentrations of test compound sufficient to reduce CPE by 50% ($EC_{50}$) or decrease cell viability by 50% ($CC_{50}$) were interpolated using standard methods in Microsoft Excel. For MCMV, the assays were run in 96 well plates in mouse embryo fibroblast cells, with drug dilutions performed as above. After a 7 d incubation, DNA was extracted and a qPCR was run to calculate drug efficacy using primers 5'-TCA GCC ATC MC TCT GCT ACC AAC-3' (SEQ ID NO: 1), 5'-ATC TGA MC AGC CGT ATA TCA TCT TG-3' (SEQ ID NO: 2), and probe 5'-TTC TCT GTC AGC TAG CCA ATG ATA TCT TCG AGC-3' (SEQ ID NO: 3). Toxicity was measured using CTG as above. For GPCMV, the assays were run in 384 well plates in Guinea Pig Lung cells, with drug dilutions performed as above. After a 7 d incubation, DNA was extracted and a qPCR was run to calculate drug efficacy using primers 5'-GAGGTCGAGAAGCTGATAT-TGG-3' (SEQ ID NO: 4), 5'-GTCTCTTCCTATGCGGGT-TATC-3' (SEQ ID NO: 5), and probe 5'-ACGTCACTTT-GAGGGCCAACTGAT-3' (SEQ ID NO: 6). Toxicity was measured using CTG as above.

A drug is considered active in the assay if an EC50 can be determine with a selectivity index [ratio of CC50 to EC50] of at least 3. In the case of the positive control, EC50s were <4 microM and the selectivity indices were always >40 against all three viruses. As defined within the assay framework, tafenoquine was not active against any of the viruses [EC50s>6 microM and CC50s were 13-17 microM in all three cases].

Tafenoquine was also tested against RSV, MERS coronavirus and influenza A H1N1, but the drug was too cytotoxic to the cell lines used to determine whether antiviral activity was present at the level of potency associated with SARS-CoV-2.

Example 28: Assay of Tafenoquine Protection in Immunosuppressed Mice from *Aspergillus*-Induce Pneumonia Experiment 1—Assessment of the Maximum Tolerated Dose of Tafenoquine in Immunosuppressed Mice.

Tafenoquine succinate powder was supplied in the form of the commercial API used to make 100 mg ARAKODA tablets [therefore it was >99.8% pure and contain no excipients]. Four dosing solutions were prepared, and the concentrations of tafenoquine succinate were adjusted based on the mean mouse weight at the start of the study in order to achieve dosing groups of 2.5, 5, 10 and 20 mg/kg tafenoquine base respectively [note that tafenoquine succinate contains 79.6% tafenoquine base].

The dosing solutions was in the form of a tafenoquine succinate suspension in the drug vehicle. A large batch [≥1 liter] of the drug vehicle [0.2% v/v Tween 80 in 1% v/v methyl cellulose in sterile water] was prepared at least 96 h before the first dose was administered and kept refrigerated [4° C.]. During preparation, the batch of drug vehicle was stirred for sufficiently long to ensure a uniform composition [4 to 24 h of stirring with a magnetic stir bar may be required].

Dosing solutions were prepared no more than 72 h prior to the first dose. Tafenoquine powder was weighed out separately for each dosing solution. After weighing, tafenoquine was transferred into an appropriately sized, transparent tube [or equivalent] containing the desired volume of drug vehicle, and gently shaken to allow development of a uniform suspension without bubble formation. The tubes containing dosing solutions were stored at [4° C.] wrapped in aluminum foil until use. Prior to use, the dosing solutions were inverted gently as required to resuspend the tafenoquine and allowed to warm temperature. Use of transparent tubes allowed for visual confirmation that an even resuspension of the drug has had been achieved prior to dosing. The above resuspension procedure was conducted the first time 48 h prior to the first day of dosing to confirm there have been no preparation issues.

Mouse Strain—Outbred male ICR mice weighing ~28 grams were used. Mice were housed 5 per cage and had access to food and water ad libitum.

Immune Status—Standard neutropenic immunosuppression regimen in the PK/dose tolerability study was used, which was also used in the in vivo efficacy model. This regimen utilizes cyclophosphamide and cortisone acetate to render animals immunosuppressed prior to aerosolized inoculation.

Cyclophosphamide (25 mg/mL) was dissolved by the addition of sterile water to the vial. This was administered as a dose of 250 mg/kg two days prior to inoculation. A second dose of cyclophosphamide was administered at a dose of 200 mg/kg three days following inoculation (cyclophosphamide concentration 20 mg/mL).

Cortisone acetate powder was weighed out and a suspension (25 mg/mL) prepared using sterile physiologic phosphate buffered saline and 0.1% polysorbate 80. The cortisone acetate suspension was prepared immediately prior to administration to the animals and was administered subcutaneously at a dose of 250 mg/kg two days prior to pulmonary inoculation and again three days following inoculation.

To prevent bacterial super-infection and deaths in the immunosuppressed mice, mice received antibacterial prophylaxis consisting of enrofloxacin at 50 ppm in the mice's drinking water beginning 2 days prior to infection.

Mouse Assessment—Throughout the studies, mice were observed multiple times per day and their overall health determined. They were also weighed multiple times throughout the course of the experiments. This was done to prevent and minimize unnecessary pain and distress that may occur. Any animal that appeared moribund prior to the scheduled endpoint was euthanized. Moribund animals were identified by the following criteria:

1. Ruffled/matted fur
2. Hunched posture
3. Weight loss (e.g., >20%)
4. Hypothermia (cool to touch)
5. Irritation/wounds at injection site
6. Inability to eat or drink Any animal demonstrating >1 of these criteria was euthanized by isoflurane anesthesia followed by exsanguination and/or cervical dislocation.

Dosing and Sample Collection—Uninfected, immunosuppressed mice were administered tafenoquine at four different dose levels by oral administration beginning the day after (day −1) the first dose of immunosuppression (day −2). A placebo control group consisting of the vehicle (1%/0.2% methylcellulose/tween 80 in sterile water) was also included and was administered orally by gavage. After the dose on the seventh day, mice were humanely euthanized via isoflurane anesthesia at various time points (e.g., 0.5, 1, 2, 4, 8, 12, & 24 hrs) and blood (via cardiac puncture).

Mice were weighed throughout the course of the experiment and monitored for signs of intolerability due to tafenoquine administration. If signs of intolerability or morbidity were observed in any group before the last collection time point, mice were humanely euthanized as described above.

Results

Figure 6:
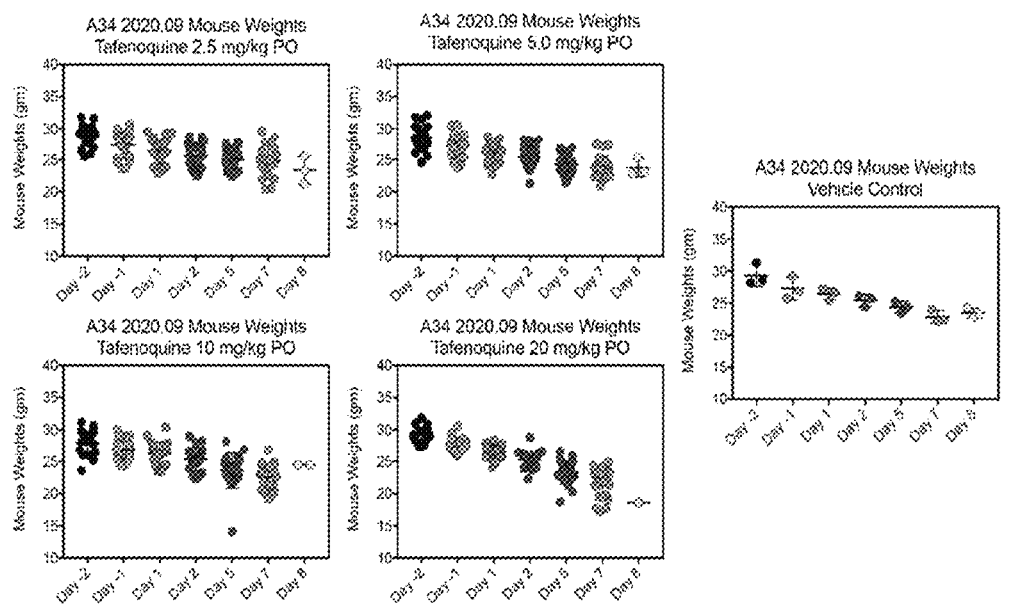
Figure 7:
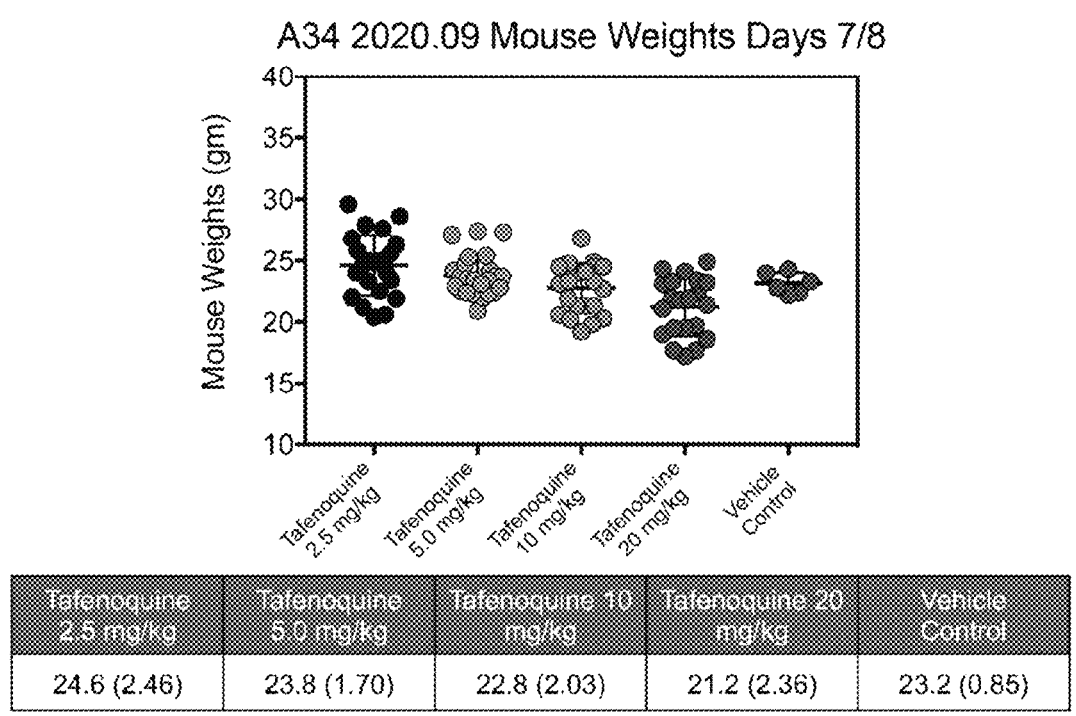
Figures 8A, 8B:
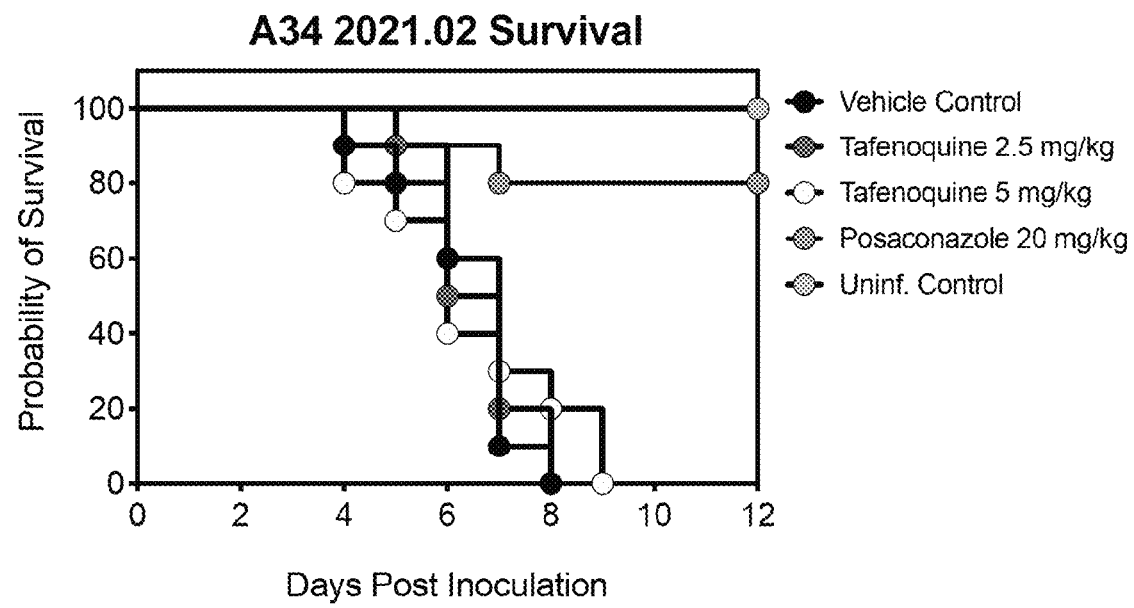

Mouse Weights—Mouse weights taken throughout the course of the experiment in the tafenoquine dose groups and vehicle control group are shown in FIG. 6 and weights specifically measured on day 7/8 are shown in FIG. 7. Reductions in mouse weights were observed across all groups throughout the time course of the study. This is consistent with what has previously observed in this model and may be attributed to the immunosuppressive regimen used. The weights on days 7/8 were numerically lower in the higher tafenoquine dose groups compared to that observed in the vehicle control group and mice administered tafenoquine at 2.5 and 5.0 mg/kg. However, these differences were not significant.

Observations—Tafenoquine was well-tolerated in the lower dosage groups (2.5 and 5.0 mg/kg), similar to what was observed in the vehicle control group. Mice appeared healthy and without signs of intolerability. However, in the higher dosage groups, there were indicators of intolerability. Mouse weights were somewhat lower on days 7/8 in these groups, and 2 of 21 in the 10 mg/kg tafenoquine group and 4 of 21 in the 20 mg/kg group were moribund prior to the study endpoint. These observations were made on days 5 and 7 in the 10 mg/kg group and on days 5, 6, 7, and 8 in the 20 mg/kg group. The 20 mg/kg group had visibly lost weight, their fur was scruffy, and mice presented in a hunched posture. The 10 mg/kg group presented with scruffy fur.

Summary—Overall, tafenoquine was well-tolerated at the two lower dosage groups in this murine model that utilized the same immunosuppression regimen for the in vivo efficacy model of invasive pulmonary aspergillosis. Some intolerability was observed in mice that received the higher tafenoquine doses of 10 mg/kg and 20 mg/kg.

Experiment 2: Assessment of Prophylactic Efficacy of Tafenoquine in *Aspergillus*-Infected Immunosuppress Mice Overview: The prophylactic efficacy of tafenoquine was evaluated as described below, with immunosuppression, monitoring of animals, preparation of tafenoquine dosing solutions, etc., being conducted in a manner identical to the toxicity study.

Isolate—*Aspergillus fumigatus* clinical isolate 293 (Af293) was the infecting organism. This isolate has been utilized previously in numerous studies and results in consistent infections in animal models (Sheppard et al., 2006, Standardization of an experimental murine model of invasive pulmonary aspergillosis. Antimicrob Agents Chemother 50:3501-3; Sheppard et al., 2004. Novel inhalational murine model of invasive pulmonary aspergillosis. Antimicrob Agents Chemother 48:1908-11; Wiederhold et al., 2008, Pyrosequencing to detect mutations in FKS1 that confer reduced echinocandin susceptibility in *Candida albicans*. Antimicrob Agents Chemother 52:4145-8). This isolate was recovered from lung tissue at autopsy from a patient with fatal invasive pulmonary aspergillosis, is also extensively used by other researchers, and was the isolate used in the *A. fumigatus* genome sequencing project.

Prior to in vivo experiments an aliquot of the Af293 stock was plated onto potato dextrose agar (PDA). The PDA plates inoculated with conidia were placed in a humidified incubator at 37° C. and allowed to germinate for 10 days prior to harvesting and preparation of conidia suspension for inoculation via the aerosol chamber. On the day of infection, PDA surfaces were flooded with sterile physiologic phosphate buffered saline containing 0.1% of the surfactant polysorbate 80 (Tween 80). The agar surfaces were then gently scraped with a disposable plastic loop. The conidial suspension was then be collected in two centrifuge tubes, and concentrated by high speed centrifugation. The conidial suspension was then diluted in sterile saline (1:1000 to 1:10,000) and the number of conidia measured by hemocytometer. The number of conidia per milliliter was then adjusted for a target starting inoculum for the murine model.

The viability of the conidia within the starting inoculum was verified by plating onto PDA and counting the number of colony-forming units. Three serial 1:100 dilutions prepared from the starting inoculum were plated (0.1 mL each) onto PDA in duplicate. The plates were incubated at 37° C. overnight and the colonies enumerated the next day. The starting inoculum consisted of at least 13 mL of conidial suspension at the desired concentration. This volume was required for a single 1 hour run of the aerosol chamber, which requires 12 mL.

Aerosol Inoculation—ICR mice were placed inside an acrylic inhalation chamber that was kept within a Class II A2 biosafety cabinet. Six milliliters of the conidial suspension was added to the Micro Mist® nebulizer and connected to the inhalation chamber and a tank of compressed air. Air was run through the nebulizer at 100 kPa, in turn driving aerosolizing conidia into the inhalation chamber, for 15 minutes. After the first 15 minutes, the remaining 6 mL of the conidial suspension was added to the nebulizer and aerosolized using 100 kPa of compressed air over 30 minutes. Once all of the conidial suspension was aerosolized, the compressed air was discontinued, and the animals were allowed to remain in the acrylic chamber for a total exposure time of 1 hour.

One hour after completing the aerosolized inoculation, 3 mice were randomly selected in order to confirm conidial delivery to the lungs. Animals were sacrificed and the lungs aseptically removed and weighed. Lungs were then placed into saline, homogenized, and serial dilutions of 1:10 and 1:100 prepared. One hundred microliters of each dilution were then plated onto PDA plates in duplicate and allowed to incubate at 37° C. for 24 hours. Colonies were then counted and the number of colony-forming units per gram of lung tissue calculated to verify delivery of conidia to the lungs.

Antifungal therapy— All treatments began two days prior to pulmonary inoculation and continued through day +7. Infected, immunosuppressed mice were administered tafenoquine at 2.5 or 5.0 mg/kg/day by oral administration beginning two days prior to infections (day −2, with Day 0 being the day of infection). A placebo control group consisting of the vehicle (1%/0.2% methylcellulose/tween 80 in sterile water) was also included and was also administered orally by gavage. A posaconazole therapy group (20 mg/kg given twice daily by oral gavage) was included as a positive control since this dose of posaconazole is protective. Also, an untreated control group was included. Survival through day 12 served as a primary endpoint, while secondary endpoint was lung fungal burden of mice sacrificed on Day +4. Lung fungal burden was determined by qPCR (Bowman, et al., 2001. Quantitative PCR assay to measure *Aspergillus fumigatus* burden in a murine model of disseminated aspergillosis: demonstration of efficacy of caspofungin acetate. Antimicrob Agents Chemother 45:3474-81 (Bowman et al., 2001)).

TABLE 8

Number of mice per time point per tafenoquine dose for the pharmacokinetic/dose tolerability experiment.

| Group | Survival Experiment | Fungal Burden Experiment |
|---|---|---|
| Placebo (Vehicle) Controls | 10 | 10 |
| Tafenoquine 2.5 mg/kg | 10 | 10 |
| Tafenoquine 5.0 mg/kg | 10 | 10 |
| Posaconazole 20 mg/kg (BID) | 10 | 10 |
| Uninfected immunosuppressed controls | 5 | 5 |
| Inoculum verification mice | 3 | 3 |
| Total Animals | 48 | 48 |

TABLE 8-continued 96 mice were used for the fungal burden and survival arms.

Survival—In the survival arm, antifungal therapy continued through day 7 post-inoculation and mice were followed off therapy until day 12.

Fungal Burden—In the tissue burden analysis of each experiment, antifungal therapy continued through day 7 post-inoculation. In the fungal burden arm, all mice were humanely euthanized as described above on day 8 and the lungs from each animal were collected. Colony-forming units were used to measure tissue fungal burden. In addition, lungs were also collected for moribund animals in the survival arm as they succumb to infection and at the pre-specified endpoint (day 12 post-inoculation). Tissue collected from each animal was weighed and placed into sterile saline containing gentamicin (25 μg/mL) and chloramphenicol (400 μg/mL) and homogenized. Serial 10-fold dilutions of the homogenates were prepared and plated onto potato dextrose agar. Following 48 hours of incubation, colonies were counted and the number of colony-forming units per gram of lung tissue was calculated for each animal. In addition, real-time PCR was also used to measure pulmonary fungal burden as previous studies have shown this to be an appropriate assay for quantifying fungal burden following echinocandin therapy against IPA (Bowman et al., 2001; Wederhold, et al., 2004. Pharmacodynamics of caspofungin in a murine model of invasive pulmonary aspergillosis: evidence of concentration-dependent activity. J Infect Dis 190:1464-71).

Data Analysis—Survival was plotted by Kaplan-Meier analysis, and differences in median survival time and the percent survival among groups was analyzed by the log-rank test and Fisher's exact test, respectively. Differences in pulmonary fungal burden were assessed for significance by analysis of variance with Tukey's post-test for multiple comparisons. A p-value of $\leq 0.05$ was considered statistically significant for all comparisons.

Results and Implications—There were no statistical differences in survival between the tafenoquine dosing groups and the vehicle control [FIG. 8A and FIG. 8B]. There was a dose-related, albeit non-statistically significant trend towards reduced fungal burden following tafenoquine treatment [FIG. 9A and FIG. 9B].

These data suggest that in this model, in which the MIC in vitro of tafenoquine against the test organism in media not containing added protein or cellular components is 16 μg/ml, that tafenoquine may moderately decrease pathogen burden without providing clinical benefit at achievable doses. It is possible that similar results would be observed in similar models for Mycobacteria, Gram positive bacteria, and fungi, for which MIC of tafenoquine is 16 ug/ml in media without added protein or cellular components.

However, since the MIC of tafenoquine against *Pneumocystis* is 10 μg/ml in media containing protein, and would be equivalent to an MIC of 5 μg/ml in the absence of protein [see Examples 1, 3, 5, 6, 12, 15, and 26], and since tafenoquine does exhibit efficacy against *Pneumocystis* in vivo, we would anticipate a therapeutic effect of tafenoquine [alone or in combination with second agent(s), such as drug(s)] against any Mycobacteria, Gram-positive, or fungal spp for which the MIC in vitro in media containing no protein is 5 ug/ml.

The teachings of all patents, published applications, and references cited herein are incorporated by reference in their entirety for all purposes.

While this invention has been particularly shown and described with references to the example embodiments thereof, it will be understood by those skilled in the art that various changes in form and details may be made therein without departing from the scope of the invention encompassed by the appended claims.

What is claimed is:

1. A method for treating a viral lung infection, or a symptom thereof, in a human subject, said method comprising
administering to said human subject an effective amount of tafenoquine, a pharmaceutically-acceptable salt thereof, or a pharmaceutical composition comprising tafenoquine.

2. The method according to claim 1, further comprising administering a second agent.

3. The method according to claim 1, wherein the subject has the viral lung infection at the time of said administering.

4. The method according to claim 1, wherein the subject does not have a viral lung infection at the time of administering, and wherein tafenoquine, the pharmaceutically-acceptable salt thereof, or the pharmaceutical composition comprising tafenoquine is administered as prophylaxis.

5. The method according to claim 1, wherein at least seven doses of about 100 mg-600 mg are administered.

6. The method according to claim 1, wherein said administration is via oral and/or intravenous and/or intra-arterial and/or sub-lingual and/or buccal route(s).

7. The method according to claim 1, wherein said subject is symptomatic of a viral infection prior to the first administration.

8. The method according to claim 1, wherein said subject is asymptomatic of a viral infection prior to the first administration.

9. The method according to claim 1, wherein said viral lung infection is latent prior to the first administration.

10. The method according to claim 1, wherein about 100 mg to about 600 mg is administered in one or more initial dose(s).

11. The method according to claim 1, wherein about 100 mg to about 600 mg is administered in one or more initial dose(s) and in one or more subsequent dose(s).

12. The method according to claim 1, wherein three initial doses are administered once per day for three days.

13. The method according to claim 1, wherein three or four initial doses are administered.

14. The method according to claim 11, wherein the subsequent dose(s) is administered once per week.

15. The method according to claim 11, wherein the subsequent dose(s) is administered once per day.

16. The method according to claim 10, wherein the initial dose(s) is about 200 mg.

17. The method according to claim 10, wherein the initial dose(s) is about 150 mg.

18. The method according to claim 10, wherein the initial dose(s) is about 100 mg.

19. The method according to claim 11, wherein the subsequent dose(s) is about 200 mg.

20. The method according to claim 11, wherein the subsequent dose(s) is about 150 mg.

21. The method according to claim 11, wherein the subsequent dose(s) is about 100 mg.

22. The method according to claim 11, wherein the first subsequent dose is administered seven days after the last initial dose.

23. The method according to claim 11, wherein an initial doses is about 200 mg and is administered once a day for three days, and wherein a subsequent dose is about 200 mg and is administered once a week.

24. The method according to claim 11, wherein there is one subsequent dose administered approximately one week after the third initial dose.

25. The method according to claim 11, wherein there are no subsequent doses.

26. A method for treating a lung infection, or a symptom thereof, in a human subject, said method comprising administering an effective amount of tafenoquine, a pharmaceutically-acceptable salt thereof, or a pharmaceutical composition comprising tafenoquine, to a human subject in need thereof, wherein said human subject is infected with SARS-CoV-2.

27. The method of claim 26, wherein said administering is via oral and/or intravenous and/or intra-arterial and/or sub-lingual and/or buccal route(s).

28. The method according to claim 26, further comprising administering a second agent.

29. The method according to claim 26, wherein at least seven doses of about 100 mg-600 mg are administered.

30. The method according to claim 26, wherein said subject is symptomatic of the SARS-CoV-2 infection prior to the first administration.

31. The method according to claim 26, wherein said subject is asymptomatic of the SARS-CoV-2 infection prior to the first administration.

32. The method according to claim 26, wherein about 100 mg to about 600 mg is administered in one or more initial dose(s).

33. The method according to claim 26, wherein about 100 mg to about 600 mg is administered in one or more initial dose(s) and in one or more subsequent dose(s).

34. The method according to claim 26, wherein three initial doses are administered once per day for three days.

35. The method according to claim 26, wherein three or four initial doses are administered.

36. The method according to claim 33, wherein the subsequent dose(s) is administered once per week.

37. The method according to claim 33, wherein the subsequent dose(s) is administered once per day.

38. The method according to claim 32, wherein the initial dose(s) is about 200 mg.

39. The method according to claim 32, wherein the initial dose(s) is about 150 mg.

40. The method according to claim 32, wherein the initial dose(s) is about 100 mg.

41. The method according to claim 33, wherein the subsequent dose(s) is about 200 mg.

42. The method according to claim 33, wherein the subsequent dose(s) is about 150 mg.

43. The method according to claim 33, wherein the subsequent dose(s) is about 100 mg.

44. The method according to claim 33, wherein the first subsequent dose is administered seven days after the last initial dose.

45. The method according to claim 33, wherein an initial doses is about 200 mg and is administered once a day for three days, and wherein a subsequent dose is about 200 mg and is administered once a week.

46. The method according to claim 33, wherein there is one subsequent dose administered approximately one week after the third initial dose.

47. The method according to claim 33, wherein there are no subsequent doses.

* * * * *